United States Patent [19]
Bales et al.

[11] Patent Number: 6,077,852
[45] Date of Patent: Jun. 20, 2000

[54] TREATMENT OF CENTRAL NERVOUS SYSTEM DISORDERS WITH SELECTIVE ESTROGEN RECEPTOR MODULATORS

[75] Inventors: Kelly Renee Bales, Cloverdale; Henry Uhlman Bryant, Indianapolis; Steven Marc Paul, Carmel; Mary Patricia Knadler, Indianapolis, all of Ind.

[73] Assignee: Eli Lilly and Company, Indianapolis, Ind.

[21] Appl. No.: 09/057,723

[22] Filed: Apr. 9, 1998

Related U.S. Application Data

[60] Provisional application No. 60/043,117, Apr. 9, 1997.

[51] Int. Cl.$^7$ .................................................. A01N 43/40
[52] U.S. Cl. .......................... 514/319; 514/324; 514/325; 514/443; 514/444; 514/445; 514/878; 514/879
[58] Field of Search ...................................... 514/319, 324, 514/325, 443, 444, 445, 878, 879

[56] References Cited

U.S. PATENT DOCUMENTS

| | | | |
|---|---|---|---|
| 3,293,263 | 12/1966 | Lednicer | 546/205 |
| 3,320,271 | 5/1967 | Lednicer | 548/570 |
| 3,394,125 | 7/1968 | Crenshaw | 548/525 |
| 3,413,305 | 11/1968 | Crenshaw | 548/525 |
| 3,862,232 | 1/1975 | Lednicer | 564/324 |
| 4,117,128 | 9/1978 | Brenner | 424/248.5 |
| 4,133,814 | 1/1979 | Jones et al. | 546/202 |
| 4,230,862 | 10/1980 | Suarez et al. | 546/237 |
| 4,418,068 | 11/1983 | Jones | 514/320 |
| 4,910,212 | 3/1990 | Boyle et al. | 514/383 |
| 5,013,761 | 5/1991 | Beedle et al. | 514/650 |
| 5,223,510 | 6/1993 | Gubin et al. | 514/299 |
| 5,254,568 | 10/1993 | Kapil et al. | 514/320 |
| 5,384,332 | 1/1995 | Fontana | 514/648 |
| 5,389,670 | 2/1995 | Fontana | 514/443 |
| 5,434,166 | 7/1995 | Glasebrook | 514/317 |
| 5,439,931 | 8/1995 | Sales | 514/443 |
| 5,462,950 | 10/1995 | Fontana | 514/324 |
| 5,470,854 | 11/1995 | von Angerer et al. | 514/233.5 |
| 5,488,058 | 1/1996 | Palkowitz | 514/324 |
| 5,492,922 | 2/1996 | Palkowitz | 514/324 |
| 5,508,292 | 4/1996 | Sall et al. | 514/324 |
| 5,510,357 | 4/1996 | Palkowitz | 514/324 |
| 5,510,358 | 4/1996 | Palkowitz | 514/324 |
| 5,510,498 | 4/1996 | Palkowitz | 549/52 |
| 5,512,296 | 4/1996 | Cullinan | 424/451 |
| 5,534,526 | 7/1996 | Cullinan | 514/324 |
| 5,550,150 | 8/1996 | Fontana | 514/443 |
| 5,552,415 | 9/1996 | May | 514/324 |
| 5,574,190 | 11/1996 | Palkowitz | 568/440 |
| 5,576,337 | 11/1996 | Bruns, Jr. et al. | 514/324 |
| 5,578,613 | 11/1996 | Bryant et al. | 514/324 |
| 5,578,614 | 11/1996 | Bryant et al. | 514/324 |
| 5,663,184 | 9/1997 | Bryant et al. | 514/324 |
| 5,686,476 | 11/1997 | May | 514/324 |
| 5,723,474 | 3/1998 | Palkowitz | 514/324 |
| 5,731,342 | 3/1998 | Cullinan et al. | 514/443 |

FOREIGN PATENT DOCUMENTS

| | | |
|---|---|---|
| 0 124 369 | 11/1984 | European Pat. Off. . |
| 0 663 209 A2 | 7/1995 | European Pat. Off. . |
| 0729 956 A1 | 2/1996 | European Pat. Off. . |
| WO 93/10113 | 5/1993 | WIPO . |
| WO 95/10513 | 4/1995 | WIPO . |

OTHER PUBLICATIONS

Fisher et al., J. National Cancer Institute, 86:527–537 (1994).
Cummings, et al., JAMA, 281:2189–2197 (1999).
Palkowitz, et al., J. Med. Chemistry, 40: 1407–1416 (1997).
"Women on Estrogen Appear at Less Risk of Alzheimer's", Indianapolis, Star, Nov. 10, 1993.
"New Alzheimer's Therapy Suggested", *Science*, 260, 1719–1720 (Jun. 18, 1993).
Crenshaw, R. R., et al., *J. Med. Chem.*, 14 (12) :1185–1190 (1971).
Durani, N., et al., *Indian J. Chem.*, 22B:489–490 (1983).
Jones, C. D., et al., *J. Med. Chem.*, 35:931–938 (1992).
Lednicer, D., et al., *J. Med. Chem.*, 8:52–57 (1964).
Jones, et al., *J. Med. Chem.*, 27:1057–66 (1984).
Madesclaire, M., *Tetrahedren*, 42 (20) :5459–5495 (1986).
Trost, B. M., et al., *Tetrahedren Letters*, 22 (14) :1287–1290.
Drabowicz, J., et al., *Synthetic Communications*, 11 (12) :1025–1030 (1981).
Kramer, J. B., et al., 34$^{th}$ National Organic Symposium, Williamsburg, VA. (Jun. 11–15, 1995).
Wyngaarden, et al., *Cecil Textbook of Medicine*, 16:1271 (1983).

*Primary Examiner*—Frederick Krass
*Attorney, Agent, or Firm*—William R. Boudreaux

[57] ABSTRACT

The present invention provides a method of treating depression, mood swings, or Alzheimer's disease in a patient in need of such treatment by administering a selective estrogen receptor modulating compound of the formula

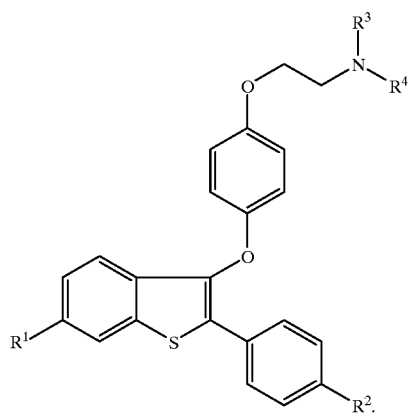

in which $R^1$ and $R^2$ are independently hydroxy and alkoxy of one to four carbon atoms; and $R^3$ and $R^4$ are independently methyl or ethyl, or $R^3$ and $R^4$, taken together with the nitrogen atom to which they are attached, form a pyrrolidino, methyl-pyrrolidino, dimethylpyrrolidino, piperidino, morpholino, or hexamethyleneimino ring.

5 Claims, No Drawings

TREATMENT OF CENTRAL NERVOUS SYSTEM DISORDERS WITH SELECTIVE ESTROGEN RECEPTOR MODULATORS

This application claims the benefit of U.S. Provisional Application Ser. No. 60/043,117, filed Apr. 9, 1997.

TECHNICAL FIELD

The present application relates to medical methods of treatment. More particularly, the present invention concerns the use of a class of substituted benzo[b]thiophene compounds for the treatment of depression, mood swings, and Alzheimer's disease in patients in need thereof.

BACKGROUND OF THE INVENTION

In addition to the well documented effects of estrogen on reproductive tissue, bone and cholesterol metabolism in post-menopausal women, it is known that estrogen has a number of actions in the central nervous system with both somatic and behavioral consequences.

In climacteric women, anxiety, depression, tension and irritability begin during the perimenopause and can be a correlated to reduced estrogen levels. Estrogen replacement therapy has been recommended for the treatment of these symptoms (cf. J. Malleson, *Lancet*, 2: 158 (1953) and R. Wilson, et al., *J. Am. Geriatric Soc.*, 11:347 (1963)).

The mechanism for the protective effects of estrogen against depression and mood swings is not well understood, but may be related to the potential effects of estrogen on biogenic amines such as serotonin (cf. M. Aylward, *Int. Res. Communications System Med. Sci.*, 1: 30 (1973).

In the area of memory and cognition enhancement, S. Phillips, et al., *Psychoneuroendocrinology*, 17: 485–495 (1992) have reported that in surgically menopausal women given estrogen, scores in immediate and delayed recall tests are greater than in similar women not given estrogen. In a prospective cohort study in post-menopausal women, A. H. Paganini-Hill, et al., *Am. J. Epidemiol.*, 140(3): 256–261 (1994) demonstrated that the risk of Alzheimer's disease was less in estrogen users as compared with women who did not use estrogen. Furthermore, the risk of Alzheimer's disease decreased significantly with increasing doses of estrogen and increased duration of estrogen use.

All of the these studies have lead to the growing perception in the literature that estrogen replacement therapy is a promising treatment for central nervous system disorders such as depression and mood swings and of Alzheimer's disease in post-menopausal women. These promising uses of estrogen replacement therapy are off-set, however, by the disadvantages of long-term estrogen therapy associated with the risks of developing reproductive tissue cancers.

Women on estrogen replacement therapy develop endometrial cancer at rates three to six times higher than nonusers after three to six years of use; after ten years on estrogen replacement therapy, the risk ratio increases to tenfold. A growing body of literature suggests that long-term (i.e. 10–15 years) causes a thirty to fifty percent increase in the risk of breast cancer.

Thus, there is a need for the development of compounds which are alternatives to estrogen possessing the same beneficial effects on depression and mood swings and on the treatment of Alzheimer's disease, but which lack the detrimental effects on reproductive tissue.

BRIEF SUMMARY OF THE INVENTION

In accordance with the present invention, there is provided a method of treating in a patient in need of such treatment, a central nervous system disorder selected from depression, mood swings, and Alzheimer's disease comprising administering a therapeutically effective amount of a compound having the structure

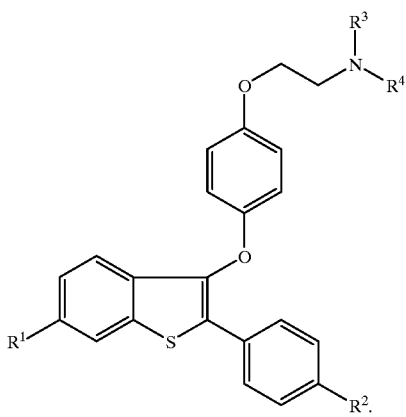

or a pharmaceutically acceptable salt or pro-drug thereof.

In the structure shown above, $R^1$ and $R^2$ are independently selected from the group consisting of hydroxy and alkoxy of one to four carbon atoms.

$R^3$ and $R^4$ are independently selected from methyl or ethyl, or $R^3$ and $R^4$, taken together with the nitrogen atom to which they are attached, form a pyrrolidino, methylpyrrolidino, dimethylpyrrolidino, piperidino, morpholino, or hexamethyleneimino ring.

The compounds of the present invention are selective estrogen receptor modulators (SERM's), that is, compounds which produce estrogen agonism in one or more desired target tissues while producing estrogen antagonism and/or minimal (i.e. clinically insignificant) agonism in reproductive tissue such as the breast or uterus.

DETAILED DESCRIPTION

Throughout this specification and the appended claims, general terms bear their usual meanings.

The term "alkyl" denotes a monovalent radical derived by removal of one hydrogen atom from methane, ethane, or a straight or branched hydrocarbon and includes such groups as methyl, ethyl, propyl, iso-propyl, n-butyl, sec-butyl, iso-butyl, tert-butyl and the like.

"Alkoxy" means an alkyl group, as defined above, attached to the parent molecular moiety through an oxygen atom and includes such groups as methoxy, ethoxy, propoxy, iso-propoxy, n-butoxy, sec-butoxy, iso-butoxy, tert-butoxy and the like. In the present invention, methoxy is the preferred alkoxy group.

The term "pro-drug," as used herein means a compound of the present invention bearing a group which is metabolically cleaved in a human to produce a therapeutically active compound of the present invention. In particular, such pro-drug compounds include those in which either or both of the substituent groups $R^1$ and $R^2$ of the structure shown above are hydroxy groups which have been protected by a pharmaceutically acceptable hydroxy protecting group which is metabolically cleaved in the body to yield a corresponding monohydroxy or dihydroxy compound of the present invention. Hydroxy protecting groups are described in Chapter 2 of T. W. Greene, et al., "Protective Groups in Organic Synthesis," Second Edition, John Wiley & Sons, Inc., New York, 1991. Simple ether and ester groups are preferred as pro-drug hydroxy protecting groups.

The term "patient" refers to a mammal which is in need of treatment for mood swings, depression or Alzheimer's disease. It is understood that guinea pigs, dogs, cats, rats, mice, hamsters, rabbits and primates, including humans, both male and female, are examples of patients within the scope of the meaning of the term.

Preferred compounds of the present invention include 6-hydroxy-2-(4-hydroxyphenyl)-3-[4-(2-piperidinoethoxy)phenoxy]benzo[b]thiophene or a pharmaceutically acceptable salt or pro-drug thereof; and 6-hydroxy-2-(4-methoxyphenyl)-3-[4-(2-piperidinoethoxy)phenoxy]benzo[b]thiophene or a pharmaceutically acceptable salt or pro-drug thereof.

Preparation of Compounds of the Invention

The starting material for one route for preparing compounds of the present invention is prepared essentially as described by C. D. Jones in U.S. Pat. Nos. 4,418,068, and 4,133,814. The starting materials have the formula 1:

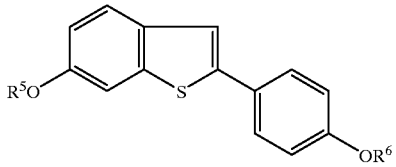

wherein $R^5$ and $R^6$ are independently —H or a hydroxy protecting group.

The $R^5$ and $R^6$ hydroxy protecting groups are moieties which are intentionally introduced during a portion of the synthetic process to protect a group which otherwise might react in the course of chemical manipulations, and is then removed at a later stage of the synthesis. Since compounds bearing such protecting groups are of importance primarily as chemical intermediates (although some derivatives also exhibit biological activity), their precise structure is not critical. Numerous reactions for the formation, removal, and reformation of such protecting groups are described in a number of standard works including, for example, *Protective Groups in Organic Chemistry,* Plenum Press (London and New York, 1973); Greene, T. W., *Protective Groups in Organic Synthesis,* Wiley (New York, 1981); and *The Peptides,* Vol. I, Schrooder and Lubke, Academic Press, (London and New York, 1965).

Representative hydroxy protecting groups include, for example, —$C_1$-$C_4$ alkyl, —$C_1$-$C_4$ alkoxy, —CO—($C_1$-$C_6$ alkyl), —$SO_2$—($C_4$-$C_6$ alkyl), and —CO—Ar in which Ar is benzyl or optionally substituted phenyl. The term "substituted phenyl" refers to a phenyl group having one or more substituents selected from the group consisting of $C_1$-$C_4$ alkyl, $C_1$-$C_4$ alkoxy, hydroxy, nitro, halo, and tri(chloro or fluoro) methyl. The term "halo" refers to bromo, chloro, fluoro, and iodo.

For compounds of formula 1, preferred $R^5$ and $R^6$ substituents are methyl, isopropyl, benzyl, and methoxymethyl. Compounds in which $R^5$ and $R^6$ each are methyl are prepared via the procedure described in the above-referenced Jones patent.

Compounds of formula 1 are also prepared in which the $R^5$ hydroxy protecting group is selectively removed, leaving $R^6$ as a hydroxy protecting group as part of the final product. The same is true in the case in which the $R^6$ hydroxy protecting group is selectively removed, leaving the $R^5$ hydroxy protecting group in place. For example, $R^5$ can be isopropyl or benzyl and $R^6$ methyl. The isopropyl or benzyl moiety is selectively removed via standard procedures, and the $R^6$ methyl protecting group is left as part of the final product.

As shown in Reaction Scheme I, the first steps of the present process for preparing certain compounds of the present invention include selectively placing a leaving group, $R^7$ at the 3 position of a compound of formula 1, to form a compound of formula 2, coupling the product of that reaction with a 4-(protected-hydroxy)phenol, 3, to form a compound of formula 4, and selectively removing the $R^8$ hydroxy protecting group to form a compound of formula 5. In the sequence of steps shown in Reaction Scheme I, the hydroxy protecting groups $R^5$, $R^6$ and $R^8$ are chosen in such a manner that, in the final step, the hydroxy protecting group $R^8$ can be selectively removed in the presence of hydroxy protecting groups $R^5$ and $R^6$.

Reaction Scheme I

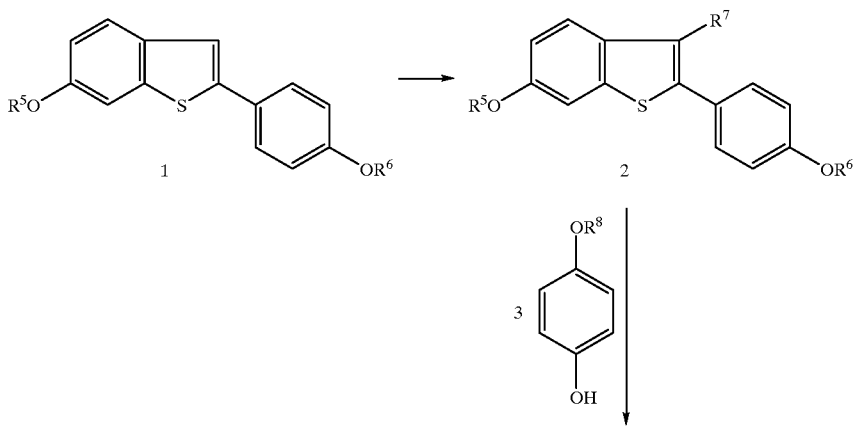

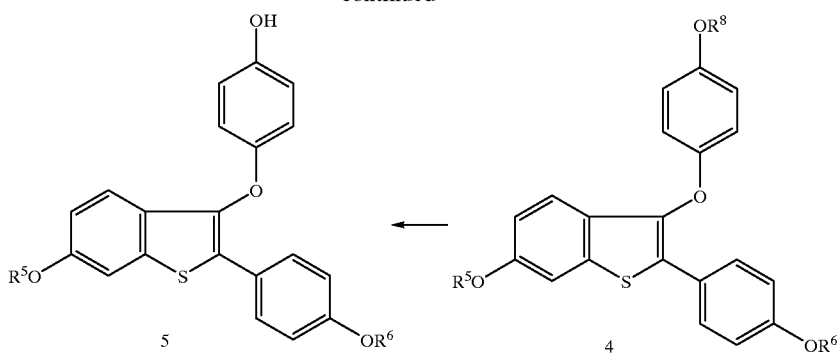

In the first step of Reaction Scheme I, an appropriate leaving group is selectively placed at the 3-position of the formula 1 starting material via standard procedures. Appropriate $R^7$ leaving groups include the sulfonates such as methanesulfonate, 4-bromobenzenesulfonate, toluenesulfonate, ethanesulfonate, isopropanesulfonate, 4-methoxybenzenesulfonate, 4-nitrobenzenesulfonate, 2-chlorobenzenesulfonate, triflate, and the like, halogens such as bromo, chloro, and iodo, and other related leaving groups. However, to insure proper placement of the leaving group, the named halogens are preferred, and bromo is especially preferred.

The present reaction is carried out using standard procedures. For example, when the preferred halogenating agents are used, an equivalent of such a halogenating agent, preferably bromine, is reacted with an equivalent of the formula 1 substrate, in a suitable solvent such as, for example, chloroform or acetic acid. The reaction is typically run at a temperature from about 40° C. to about 80° C.

The reaction product from the above process step, a compound of formula 2, is then reacted with a 4-(protected-hydroxy)phenol, 3, to form compounds of formula 4 in which $R^8$ is a selectively removable hydroxy protecting group. Generally, the 4-hydroxy protecting moiety of the phenol may be any known protecting group which can be selectively removed without removing, in this instance, the $R^5$ and, when present, $R^6$ moieties of a formula 3 compound. Preferred $R^8$ protecting groups include methoxymethyl, when $R^5$ and/or $R^6$ are not methoxymethyl, and benzyl. Of these, benzyl is especially preferred. The 4-(protected-hydroxy)phenol reactants are commercially available or can be prepared via standard procedures.

The coupling reaction between compounds of formula 2 and those of formula 3 is known in the art as an Ullman reaction and is generally run according to standard procedures [see, e.g., "Advanced Organic Chemistry: Reactions, Mechanisms, and Structure," Fourth Edition, 3–16, (J. March, ed., John Wiley & Sons, Inc. 1992); Jones, C. D., J. Chem. Soc. Perk. Trans. I, 4:407 (1992)].

In general, equivalent amounts of the two aryl substrates, in the presence of up to an equimolar amount of a copper(I) oxide catalyst and an appropriate solvent, are heated to reflux under an inert atmosphere. Preferably, an equivalent of a formula 2 compound in which $R^7$ is bromo is reacted with an equivalent amount of 4-benzyloxyphenol in the presence of an equivalent of cuprous oxide.

Appropriate solvents for this reaction are those solvents or mixture of solvents which remain inert throughout the reaction. Typically, organic bases, particularly a hindered base such as, for example, 2,4,6-collidine, are preferred solvents.

The temperature employed in this step is generally sufficient to effect completion of this coupling reaction, and will influence the amount of time required therefore. When the reaction mixture is heated to reflux under an inert atmosphere such as nitrogen, the time-to-completion is usually from about 20 to about 60 hours.

Following coupling of a compound of formula 2 with one of formula 3, to form a formula 4 compound, formula 5 compounds are prepared by selectively removing the $R^8$ hydroxy protecting group of a formula 4 compound via well known reduction procedures. It is imperative that the selected procedure will not affect the $R^5$ and, when present, $R^6$ hydroxy protecting groups.

When $R^8$ is the preferred benzyl moiety, and $R^5$ and, when present, $R^6$ each are methyl, the present process step is carried out via standard hydrogenolysis procedures. Typically, the formula 4 substrate is added to a suitable solvent or mixture of solvents, followed by the addition of a proton donor to accelerate the reaction and an appropriate hydrogenation catalyst.

Appropriate catalysts include noble metals and oxides such as palladium, platinum, and rhodium oxide on a support such as carbon or calcium carbonate. Of these, palladium-on-carbon, particularly 10% palladium-on-carbon, is preferred. Solvents for this reaction are those solvents or mixture of solvents which remain inert throughout the reaction. Typically, ethylacetate and $C_1$–$C_4$ aliphatic alcohols, particularly ethanol, is preferred. For the present reaction, hydrochloric acid serves as an adequate and preferred proton donor.

When run at ambient temperature and a pressure ranging form about 30 psi (206.8 kilopascals) to about 50 psi 344.7 kilopascals), the present reaction runs quite rapidly. Progress of this reaction may be monitored by standard chromatographic techniques such as thin layer chromatography.

As shown in Reaction Scheme II, upon preparation of a formula 5 compound, it is reacted with a compound of formula

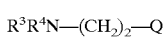

wherein $R^3$ and $R^4$ are as defined above, and Q is a bromo or, preferably, chloro, to form a compound of formula 7. The formula 7 compound is then deprotected to form a compound of formula I.

Reaction Scheme II

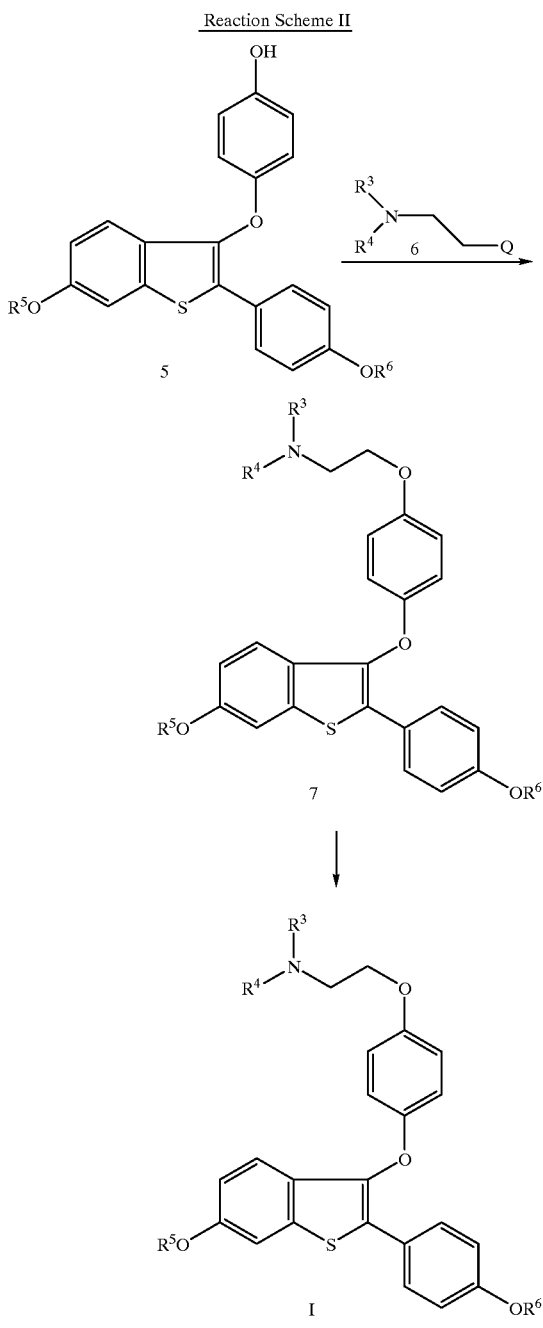

Ia, R⁵ = R⁶ = H
Ib, R⁵ = H
Ic, R⁶ = H

In the first step of the process shown in Reaction Scheme II, the reaction is carried out via standard procedures. Compounds of formula 6 are commercially available or are prepared by means well known to one of ordinary skill in the art. Preferably, the hydrochloride salt of a formula 6 compound is used. In a particularly preferred case of the compounds of the present invention, 2-chloroethylpiperidine hydrochloride, is used.

Generally, at least about 1 equivalent of a formula 5 substrate is reacted with 2 equivalents of a formula 6 compound in the presence of at least about 4 equivalents of an alkali metal carbonate, preferably cesium carbonate, and an appropriate solvent.

Suitable solvents for this reaction are those solvents or mixture of solvents which remain inert throughout the reaction. N,N-dimethylformamide, especially the anhydrous form thereof, is preferred. The temperature employed in this step should be sufficient to effect completion of this alkylation reaction. Typically, ambient temperature is sufficient and preferred. The present reaction preferably is run under an inert atmosphere, particularly nitrogen.

Under the preferred reaction conditions, this reaction will run to completion in about 16 to about 20 hours. The progress of the reaction can be monitored via standard chromatographic techniques.

In an alternative process for preparing compounds of the present invention, shown in Reaction Scheme III below, a formula 5 compound is reacted in an alkali solution with an excess of an alkylating agent of formula 8:

$$Q-(CH_2)_n-Q'$$

in which Q and Q' are the same or different leaving groups. Appropriate leaving groups are those mentioned above.

Reaction Scheme III

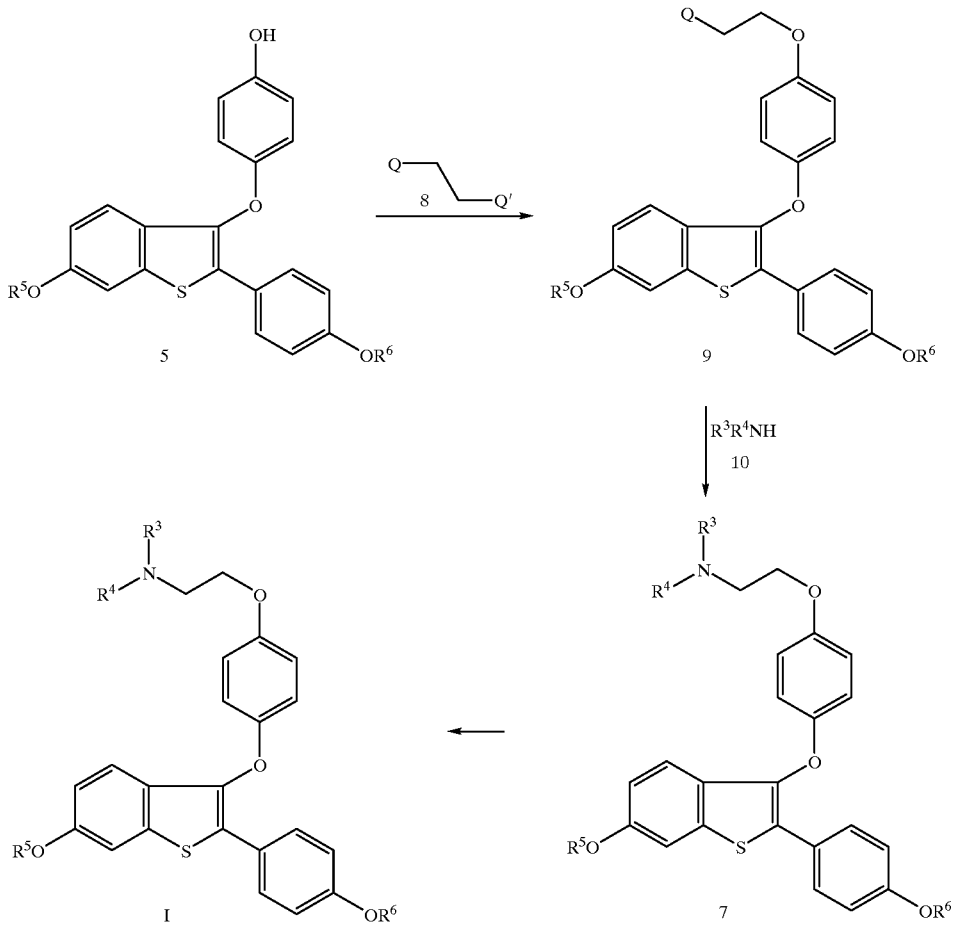

Ia, $R^5 = R^6 = H$
Ib, $R^5 = H$
Ic, $R^6 = H$

A preferred alkali solution for this alkylation reaction contains potassium carbonate in an inert solvent such as, for example, methyethyl ketone (MEK) or DMF. In this solution, the unprotected hydroxy group of the formula 5 compound is converted to a phenoxide ion which displaces one of the leaving groups of the alkylating agent.

This reaction proceeds best when the alkali solution containing the reactants and reagents is brought to reflux and allowed to run to completion. When using MEK as the preferred solvent, reaction times range from about 6 hours to about 20 hours.

The reaction product from this step, a compound of formula 9 is then reacted with a compound of formula 10 selected from 1-piperidine, 1-pyrrolidine, methyl-1-pyrrolidine, dimethyl-1-pyrrolidine, 4-morpholine, dimethylamine, diethylamine, diisopropylamine, or 1-hexamethyleneimine, via standard techniques, to form compounds of formula 7. Preferably, the hydrochloride salt of a compound of formula 10 is employed, with piperidine hydrochloride being particularly preferred. The reaction is typically carried out with the alkylated compound of formula 9 in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run for completion. The progress of this reaction step can be monitored via standard chromatographic techniques.

Certain preferred compounds of formula I are obtained by cleaving the $R^5$ and, when present, $R^6$ hydroxy protecting groups of formula I compounds via well known procedures. Numerous reactions for the formation and removal of such protecting groups are described in a number of standard works including, for example, *Protective Groups in Organic Chemistry,* Plenum Press (London and New York, 1973); Greene, T. W., *Protective Groups in Organic Synthesis,* Wiley, (New York, 1981); and *The Peptides,* Vol. I, Schrooder and Lubke, Academic Press (London and New York, 1965). Methods for removing preferred $R^7$ and/or $R^8$ hydroxy protecting groups, particularly methyl and methoxymethyl, are essentially as described in the Examples, infra.

An alternative, and preferred, method for the preparation of compounds of the present invention is shown in Reaction Scheme IV. In the process shown there, the sulfur atom of a formula 2 compound is oxidized to form a sulfoxide, 11, which is then reacted with a nucleophilic group to introduce the oxygen atom linker of formula I compounds. The sulfoxide moiety of formula 12 compounds is then reduced to provide certain compounds of the present invention.

tetrahydrofuran. Other bases that can be employed include potassium carbonate and cesium carbonate. Additionally,

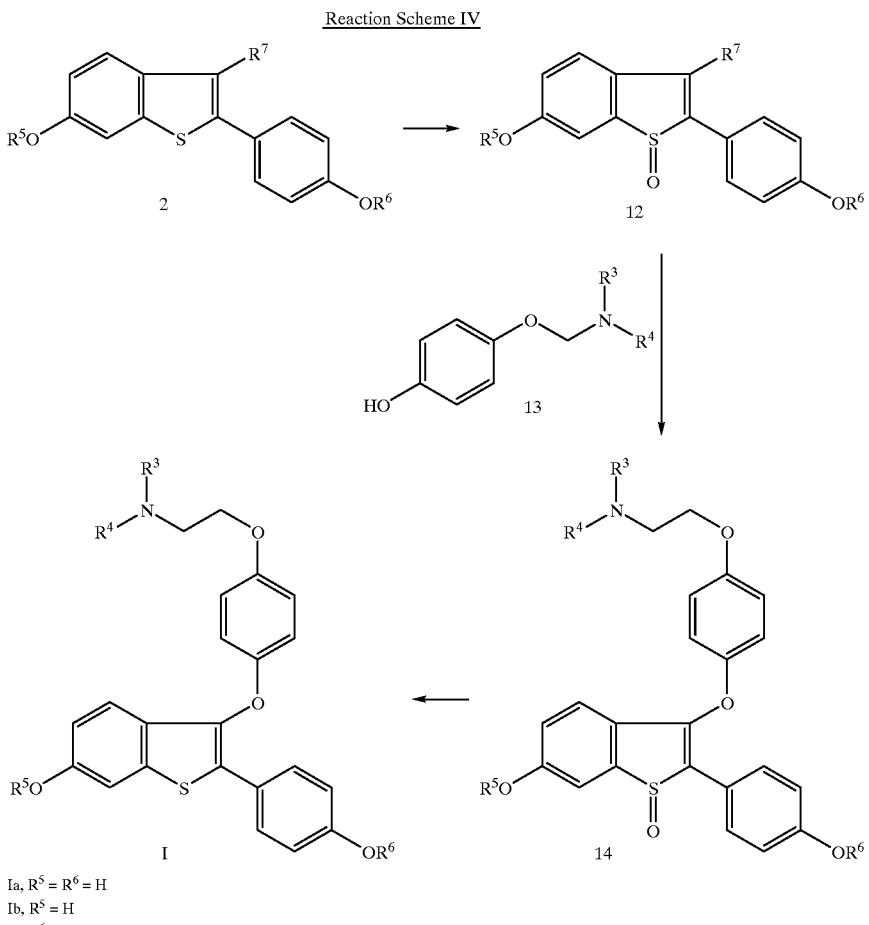

Reaction Scheme IV

Ia, $R^5 = R^6 = H$
Ib, $R^5 = H$
Ic, $R^6 = H$

In the first step of this process, a compound of formula 2 is selectively oxidized to the sulfoxide, 12. A number of known methods are available for the process step [see, e.g., Madesclaire, M., *Tetrahedron*, 42 (20); 5459–5495 (1986); Trost, B. M., et al., *Tetrahedron Letters*, 22 (14); 1287–1290 (1981); Drabowicz, J., et al., *Synthetic Communications*, 11 (12); 1025–1030 (1981); Kramer, J. B., et al., 34*th National Organic Symposium*, Williamsburg, Va., Jun. 11–15, 1995]. However, many oxidants provide only poor conversion to the desired product as well as significant over-oxidation to the sulfone. The preferred process, however, converts a formula 2 compound to a sulfoxide of formula 12 in high yield with little or no formation of sulfones. This process involves the reaction of a formula 2 compound with about 1 to about 1.5 equivalents of hydrogen peroxide in a mixture of about 20% to about 50% trifluoroacetic acid in methylene chloride. The reaction is run at a temperature from about 10° C. to about 50° C., and usually required from about 1 to about 2 hours to run to completion.

Next, the 3-position leaving group, $R^7$, is displaced by the desired nucleophilic derivative of formula 13. Such nucleophilic derivatives are prepared via standard methods.

In this step of the process, the acidic proton of the nucleophilic group is removed by treatment with a base, preferably a slight excess of sodium hydride or potassium tertbutoxide, in a polar aprotic solvent, preferably DMF or other solvents such as dioxane or dimethylsulfoxide can be employed. The deprotonation is usually run at a temperature between about 0° C. and about 30° C., and usually requires about 30 minutes for completion. A compound of formula XIV is then added to the solution of the nucleophile. The displacement reaction is run at a temperature between 0° C. and about 50° C., and is usually run in about 1 to about 2 hours. The product is isolated by standard procedures.

In the next step of the present process, the sulfoxide of formula 14 is reduced to a benzothiophene compound of formula I.

When desired, the hydroxy protecting group or groups of the products of the process shown in Reaction Scheme IV can be removed, and a salt of the product of any step of the process.

Pro-drug ester compounds of formula I are prepared by replacing the 6- and/or 4'-position hydroxy moieties, when present, with a moiety of the formula —OCO($C_1$–$C_6$ alkyl), or —OSO$_2$($C_2$–$C_6$ alkyl) via well known procedures. See, e.g., U.S. Pat. No. 4,358,593.

For example, when an —OCO($C_1$–$C_6$ alkyl) group is desired, a mono- or dihydroxy compound of formula I is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

These reactions are carried out at moderate temperatures, in the range from about −25° C. to about 100° C., frequently under an inert atmosphere such as nitrogen gas. However, ambient temperature is usually adequate for the reaction to run.

Acylation of a 6-position and/or 4'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned ester pro-drug compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

Each of the above techniques which provide —OCO ($C_1$–$C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the 6- and/or 4'-position hydroxy group of a formula I compound is converted to a group of the formula —$OSO_2(C_2$–$C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound also can be reacted with the appropriate sulfonic anhydride or mixed sulfonic anhydrides. Such reactions are carried out under conditions such as were explained above in the discussion of reaction with acid halides and the like.

Preparation of Pharmaceutically Acceptable Salts of Compounds of the Present Invention Although the free-base form of formula I compounds can be used in the medical methods of treatment of the present invention, it is preferred to prepare and use a pharmaceutically acceptable salt form. The compounds used in the methods of this invention primarily form pharmaceutically acceptable acid addition salts with a wide variety of organic and inorganic acids. Such salts are also contemplated as falling within the scope of the present invention.

The term "pharmaceutically acceptable salts" as used throughout this specification and the appended claims denotes salts of the types disclosed in the article by Berge, et al., *J. Pharmaceutical Sciences*, 66(1): 1–19 (1977). Suitable pharmaceutically acceptable salts include salts formed by typical inorganic acids such as hydrochloric, hydrobromic, hydroiodic, nitric, sulfuric, phosphoric, hypophosphoric, and the like as well as salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids. Such pharmaceutically acceptable organic acid addition salts include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluene-sulfonate, xylenesulfonate, tartarate, and the like. Preferred salts are the hydrochloride and oxalate salts.

The pharmaceutically acceptable acid addition salts are typically formed by reacting a compound of formula I with an equimolar or slight molar excess of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

Pharmaceutical Formulations

The compounds of this invention are administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention are prepared by procedures known in the art using well known and readily available ingredients. For example, the compounds of Formula I, either alone, or in combination with an estrogen or progestin compound, are formulated with common excipients, diluents, or carriers, and formed into tablets, capsules, suspensions, solutions, injectables, aerosols, powders, and the like.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

The formulations may be specially formulated for oral administration, in solid or liquid form, for parenteral injection, topical or aerosol administration, or for rectal or vaginal administration by means of a suppository.

The pharmaceutical compositions of this invention can be administered to humans and other mammals orally, rectally, intravaginally, parenterally, topically (by means of powders, ointments, creams, or drops), bucally or sublingually, or as an oral or nasal spray. The term "parenteral administration" refers herein to modes of administration which include intravenous, intramuscular, intraperitoneal, instrasternal, subcutaneous, or intraarticular injection or infusion.

Pharmaceutical compositions of this invention for parenteral administration comprise sterile aqueous or non-aqueous solutions, dispersions, suspensions, or emulsions, as well as sterile powders which are reconstituted immediately prior to use into sterile solutions or suspensions. Examples of suitable sterile aqueous and non-aqueous carriers, diluents, solvents or vehicles include water, physiological saline solution, ethanol, polyols (such as glycerol, propylene glycol, polyethylene glycol), and the like), and suitable mixtures thereof, vegetable oils (such as olive oil), and injectable organic esters such as ethyl oleate. Proper fluidity is maintained, for example, by the use of coating materials such as lecithin, by the maintenance of proper particle size in the case of dispersions and suspensions, and by the use of surfactants.

Parenteral compositions may also contain adjuvants such as preservatives, wetting agents, emulsifying agents, and dispersing agents. Prevention of the action of microorganisms is ensured by the inclusion of antibacterial and antifungal agents, for example, paraben, chlorobutanol, phenol sorbic acid, and the like. It may also be desirable to include isotonic agents such as sugars, sodium chloride, and the like. Prolonged absorption of injectable formulations may be brought about by the inclusion of agents which delay absorption such as aluminum monostearate and gelatin.

In some cases, in order to prolong the effect of the drug, it is desirable to slow the absorption of the drug following subcutaneous or intramuscular injection. This may be accomplished by the use of a liquid suspension or crystalline or amorphous material of low water solubility or by dissolving or suspending the drug in an oil vehicle. In the case of the subcutaneous or intramuscular injection of a suspension containing a form of the drug with low water solubility, the rate of absorption of the drug depends upon its rate of dissolution.

Injectable "depot" formulations of the compounds of this invention are made by forming microencapsulated matrices of the drug in biodegradable polymers such as poly(lactic acid), poly(glycolic acid), copolymers of lactic and glycolic acid, poly (orthoesters), and poly (anhydrides) these materials which are described in the art. Depending upon the ratio of drug to polymer and the characteristics of the particular polymer employed, the rate of drug release can be controlled.

Injectable formulations are sterilized, for example, by filtration through bacterial-retaining filters, or by presterilization of the components of the mixture prior to their admixture, either at the time of manufacture or just prior to administration (as in the example of a dual chamber syringe package).

Solid dosage forms for oral administration include capsules, tablets, pills, powders, and granules. In such solid dosage forms, the active component is mixed with at least one inert, pharmaceutically acceptable carrier such as sodium citrate, or dicalcium phosphate, and/or (a) fillers or extenders such as starches, lactose, glucose, mannitol, and silicic acid, (b) binding agents such as carboxymethyl-cellulose, alginates, gelatin, poly(vinylpyrrolidine), sucrose and acacia, (c) humectants such as glycerol, (d) disintegrating agents such as agar-agar, calcium carbonate, potato or tapioca starch, alginic acid, silicates and sodium carbonate, (e) solution retarding agents such as paraffin, (f) absorption accelerating agents such as quaternary ammonium compounds, (g) wetting agents such as cetyl alcohol and glycerin monostearate, (h) absorbents such as kaolin and bentonite clay, and (i) lubricants such as talc, calcium stearate, magnesium stearate, solid poly(ethylene glycols), sodium lauryl sulfate, and mixtures thereof. In the case of capsules, tablets and pills, the dosage form may also contain buffering agents.

Solid compositions of a similar type may also comprise the fill in soft or hard gelatin capsules using excipients such as lactose as well as high molecular weight poly(ethylene glycols) and the like.

Solid dosage forms such as tablets, dragees, capsules, pills and granules can also be prepared with coatings or shells such as enteric coatings or other coatings well known in the pharmaceutical formulating art. The coatings may contain opacifying agents or agents which release the active ingredient(s) in a particular part of the digestive tract, as for example, acid soluble coatings for release of the active ingredient(s) in the stomach, or base soluble coatings for release of the active ingredient(s) in the intestinal tract.

The active ingredient(s) may also be microencapsulated in a sustained-release coating, with the microcapsules being made part of a pill of capsule formulation.

Liquid dosage forms for oral administration of the compounds of this invention include solution, emulsions, suspensions, syrups and elixirs. In addition to the active components, liquid formulations may include inert diluents commonly used in the art such as water or other pharmaceutically acceptable solvents, solubilizing agents and emulsifiers such as ethanol, isopropanol, ethyl carbonate, ethyl acetate, benzyl alcohol, benzyl benzoate, propylene glycol, 1,3-butylene glycol, dimethyl formamide, oils (in particular, cottonseed, ground nut, corn, germ, olive, castor, and sesame oils), glycerol, tetrahydrofurfuryl alcohol, poly(ethylene glycols), fatty acid esters of sorbitol, and mixtures thereof.

Besides inert diluents, the liquid oral formulations may also include adjuvants such as wetting agents, emulsifying and suspending agents, and sweetening, flavoring, and perfuming agents.

Liquid suspension, in addition to the active ingredient(s) may contain suspending agents such as ethoxylated isostearyl alcohols, polyoxyethylene sorbitol and sorbitan esters, microcrystalline cellulose, aluminum metahydroxide, bentonite clay, agar-agar, and tragacanth, and mixtures thereof.

Compositions for rectal or intravaginal administration are prepared by mixing one or more compounds of the present invention with suitable non-irritating excipients such as cocoa butter, polyethylene glycol or any suppository wax which is a solid at room temperature, but liquid at body temperature and therefore melt in the rectum or vaginal cavity to release the active component(s). The compounds are dissolved in the melted wax, formed into the desired shape, and allowed to harden into the finished suppository formulation.

Compounds of the present invention may also be administered in the form of liposomes. As is know in the art, liposomes are generally derived from phospholipids or other lipid substances. Lipososome formulations are formed by mono- or multilamellar hydrated liquid crystals which are dispersed in an aqueous medium. Any non-toxic, pharmaceutically acceptable, and metabolizable lipid capable of forming liposomes can be used. The present compositions in liposome form can contain, in addition to one or more active compounds of the present invention, stabilizers, excipients, preservatives, and the like. The preferred lipids are phospholipids and the phosphatidyl cholines (lecithins), both natural and synthetic.

Methods for forming liposomes are know in the art as described, for example, in Prescott, Ed., *Methods in Cell Biology*, Volume XIV, Academic Press, New York, N.Y. (1976), p. 33 et seq.

Method of the Present Invention

As discussed above, estrogen has a beneficial effect on mood swings and depression in post-menopausal women and has been credited with also having a beneficial effect in memory and cognition in elederly patients. To be used as a therapeutic agent for such conditions, it may be necessary to administer a drug to a patient over an extended period of time. However, the drawbacks associated with the long-term use of estrogen and the risk of attendant reproductive tissue cancers mitigate against such long-term use of estrogen. A substitute for estrogen must have the beneficial effects of estrogen in the brain without the associated detrimental effects in the breast and uterus. Moreover, such a substitute must be capable of crossing the blood-brain barrier in order to exert the desired effect.

The compounds of the present invention possess the desired profile, being selective estrogen receptor modulators (SERM's) with estrogen-like effects in certain tissues while lacking (or having minimal agonistic effect) in the breast and uterus. Moreover, as demonstrated by the following data, certain compounds of the present invention have been found to cross the blood-brain barrier and to have effective levels in brain following oral administration in laboratory animals.

Distribution of Compounds of the Invention Among Various Tissues in the Female F344 Rat Female Fischer 344 rats (approximately twelve weeks old) were given a single oral gavage dose of 5 mg/kg (30 mCi/kg) of $^{14}$C-labeled 6-hydroxy-2-(4-methoxyphenyl)-3-[4-(piperidinoethoxy)phenoxy]benzo[b]thiophene hydrochloride in 50% PEG 300/50% water. Blood and tissues were collected from three rats at each time point: just prior to dosing and at 2, 4, 8, and 24 hours after dosing. At each time point, the animals were sacrificed, blood samples were collected and the heparinized blood was centrifuged and the plasma obtained. Following collection of the bloood sample in each case, the animals were perfused with 0.9% saline solution and the brain, pituitary, femurs, ovaries, uterus and liver were surgically removed and placed in separate containers. The brain was further divided into the hypothalamus, hippocampus, cerebellum, and cerebral cortex. All samples were stored at −70° C.

The radioactivity of each sample was determined by liquid scintillation spectrometry. Plasma was counted directly, while the other tissues were either homogenized, digested, or oxidized prior to liquid scintillation counting. All tissues were weighed prior to treatment. The liver and cerebrum were homogenized in 0.9% saline solution and an aliquot of the homgenate was oxidized. The pituitary, hippocampus, hypothalamus, ovaries, uterus and cerebellum were oxidized directly after drying. The femur was digested with a mixture of 30% hydrogen peroxide, and concentrated perchloric acid (2/1 v/v) prior to liquid scintillation counting.

Samples were oxidized on a Packard Model307 Oxidizer and the resulting $^{14}CO_2$ trapped for liquid scintillation counting. The radioactivity in each tissue sample was converted to nanogram equivalents per gram of tissue (specific activity=16.3 dpm/ng). The 0–24 hour area under the curve ($AUC_{0-24}$ hr) was calculated for each sample.

A liver and cerebral cortex homogenate were analyzed by HPLC and UV detection at 315 nm to determine if the radioactivity in these tissues was actually due to the drug initially dosed, to the primary metabolite, 6-hydroxy-2-(4-hydroxyphenyl)-3-[4-(piperidinoethoxy)phenoxy]-benzo[b] thiophene, or there glucuronide conjugates. The cerebral cortex sample was obtained eight hours after dosing and the liver samples were collected at four and eight hours after dosing. The proteins in the homogenate were precipitated with acetonitrile and the supernate was evaporated to dryness. The residue was reconstituted in mobile phase and injected onto a SynChropak SCD-100 column with the initial mobile phase composed of 60% 0.05 M $KH_2PO_4$, pH 7/17% methanol/17% acetonitrile. (v/v/v). The retention times of the peaks from the homogenate were compared with those obtained from authentic samples of 6-hydroxy-2-(4-methoxyphenyl)-3-[4-(piperidinoethoxy)-phenoxy] benzo[b]thiophene and its metabolite, 6-hydroxy-2-(4-hydroxyphenyl)-3-[4-(piperidinoethoxy)phenoxy]benzo[b]-thiophene.

Radioactivity was found in all tissues as shown by the data presented in Table 1.

TABLE 1

Mean Pharmakokinetic Parameters for Radioactivity after a Single Oral Dose of $^{14}$C-6-hydroxy-2- (4-methoxyphenyl) -3- [4-(piperidinoethoxy) phenoxy]benzo [b] -thiophene to Female F344 Rats

| TISSUE | $C_{max}$* (ng/ml) | $T_{max}$ (hr) | AUC* (ng hr/mL) |
|---|---|---|---|
| Plasma | 53 ± 6 | 7 | 653 ± 28 |
| Cerebellum | 425 ± 25 | 8 | 5442 ± 456 |
| Cerebrum | 488 ± 37 | 8 | 6259 ± 560 |
| Femur | 523 ± 193 | 8 | 6458 ± 1666 |
| Hippocampus | 517 ± 37 | 8 | 7024 ± 660 |
| Uterus | 609 ± 31 | 7 | 8093 ± 311 |
| Hypothalamus | 689 ± 112 | 8 | 8310 ± 1295 |
| Ovaries | 1321 ± 187 | 7 | 16761 ± 1785 |
| Pituitary | 3203 ± 608 | 8 | 37666 ± 8829 |
| Liver | 3839 ± 669 | 7 | 51913 ± 3126 |

Examination of the data appearing in Table 1 indicate that radioactive material was found in all tissues, with peak levels being reached at 8 hours after dosing, with the exception of the liver where peak levels were reached at 4 hours after dosing. The lowest concentrations were found in plasma and the highest in the liver. Both the $C_{max}$ and $AUC_{0-24\ hr}$ of radioactivity for the cerebellum, cerebrum, hippocampus, and hypothalamus were greater than those observed in the plasma, indicating that radioactivity distributed into the brain areas after administration of the parent compound, $^{14}$C-6-hydroxy-2-(4-methoxyphenyl)-3-[4-(piperidinoethoxy)phenoxy]benzo[b]thiophene. Analysis of the cerebral cortex homogenate (described above) showed that the radioactivity was due both to the parent compound, $^{14}$C-6-hydroxy-2-(4-methoxyphenyl)-3-[4-(piperidinoethoxy)phenoxy]benzo[b]thiophene and its dihydroxy metabolite, $^{14}$C-6-hydroxy-2-(4-hydroxyphenyl)-3-[4-(piperidinoethoxy)phenoxy]benzo[b]thiophene, in a ratio of approximately 4:1. Peaks corresponding to the glucuronide conjugates of either the parent compound or its dihydroxy metabolite were not observed in the HPLC chromatogram of the cerebral cortex homogenate. The HPLC chromatogram of the liver homogenates did, however, show peaks whose retention times corresponded to the parent compound and its glucuronide conjugate.

Similarity of 6-hydroxy-2-(4-methoxyphenyl)-3-[2-(piperidino-ethoxy)phenoxy]benzo[b]thiophene to estrogen in the hippo-campus Estrogens, such as 17b-estradiol, regulate gene transcription by binding to estrogen receptors (ER) which reside in the cytoplasm of certain cell populations. Ligand activation of the ER is a prerequisite for nuclear transport of the complex where binding to a 13 base-pair palindromic DNA consensus sequence (estrogen response element, or ERE) begins assembly of a transcriptional apparatus which culminates in the activation of appropriate target genes. A variety of genes have been identified which are regulated by estrogen. These include cytoskeletal proteins, neurotransmitter biosynthetic and metabolic enzymes and receptors, as well as other hormones and neuropeptides. ERE's have been identified in many estrogen-responsive genes including vitellogenin, c-fos, prolactin, and luteinizing hormone.

Of significance in the central nervous system, ERE-like sequences have been identified in $p75^{ngr}$ and trkA, both of which serve as signaling molecules for the neurotrophins: nerve growth factor (NGF), brain derived nerve growth factor (BDNGF), and neurotrophin-3.

BDNF as well as NGF have been shown to promote the survival of cholinergic neurons in culture. It is postulated that if the interactions between neurotrophins and estrogens are important for the development and survival of basal forebrain neurons (which degenerate in Alzheimer's disease) then clinical conditions in which an estrogen deficiency exists (as after menopause) may contribute to a loss of thses neurons.

A commonly employed model of estrogen depletion is the ovariectomized adult rat. An experiment was conducted in ovariectomized rats using differential mRNA display to determine the similarities and/or differences between a representative compound of the present invention, 6-hydroxy-2-(4-methoxyphenyl)-3-[4-(2-piperidinoethoxy)phenoxy]-benzo[b]thiophene, and estrogen at affecting gene expression in various brain regions. Specifically, female Sprague-Dawley rats, 6 weeks of age, were ovariectomized by the vendor. Following one week of acclimation to the laboratory facility, daily subcutaneous injections of estradiol benzoate (0.03 mg/kg) or 6-hydroxy-2-(4-methoxyphenyl)-3-[4-(2-piperidinoethoxy)phenoxy]-benzo [b]thiophene (1 mg/kg), or vehicle (control) were initiated.

After five weeks of daily treatment, animals were sacrificed and their brains removed and hippocampi collected by microdissection. The hippocampi were fast frozen in liquid nitrogen and stored at $-70°$ C. Total RNA was prepared from pooled tissue from the appropriate treatment and control groups and reverse transcribed using a 3' oligonucleotide primer which selected for specific mRNA (poly-A+) populations. Polymerase chain reactions (PCR) were carried out in a cocktail consisting of: random 5' oligonucleotides (10 base-pairs in length; total of 150), reaction buffer, Taq polymerase, and a $^{32}$PdTCP.

After 40 rounds of amplification, the reaction products were size fractionated on a 6% TBE-urea gel, dried and exposed to x-ray film. The resulting MRNA display patterns were compared between treatment groups. 6-Hydroxy-2-(4-methoxyphenyl)-3-[4-(2-piperidinoethoxy)phenoxy]benzo [b]-thiophene produced a parallel pattern of gene activation or inactivation in the rat himmpocampus as that observed for estrogen. These data indicate that 6-hydroxy-2-(4-methoxyphenyl)-3-[4-(2-piperidinoethoxy)phenoxy]benzo [b]-thiophene produced an estrogen-like effect in the hippocampus, a key brain region associated with Alzheimer's disease in humans.

Thus, administration of an effective amount of a compound of the present invention, especially 6-hydroxy-2-(4-methoxyphenyl)-3-[4-(2-piperidinoethoxy)phenoxy]benzo[b]-thiophene and its primary metabolite, 6-hydroxy-2-(4-hydroxyphenyl)-3-[4-(2-piperidinoethoxy)phenoxy]benzo[b]-thiophene would be useful in the treatment of Alzheimer's disease in a human patient.

As used herein, the term "effective amount" means an amount of compound of the present invention which is capable of alleviating the symptoms of the conditions herein described. The specific dose of a compound administered according to this invention is determined by the particular circumstances surrounding the case including, for example, the potency of the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The exact dose is determined, in accordance with the standard practice in the medical arts of dose titrating the patient; that is, initially administering a low dose of the compound, and gradually increasing the does until the desired therapeutic effect is observed.

The following examples are presented to further illustrate the preparation of compounds of the present invention. The Examples are not to be read as limiting the scope of the invention as it is defined by the appended claims.

NMR data for the following Examples were generated on a GE 300 MHz NMR instrument, and anhydrous hexadeutero-dimethylsulfoxide was used as the solvent unless otherwise indicated.

EXAMPLE 1

Preparation of [6-methoxy-3-[4-[2-(1-piperidinyl)ethoxy]-phenoxy]-2-(4-methoxyphenyl)]benzo[b]thiophene oxalate salt

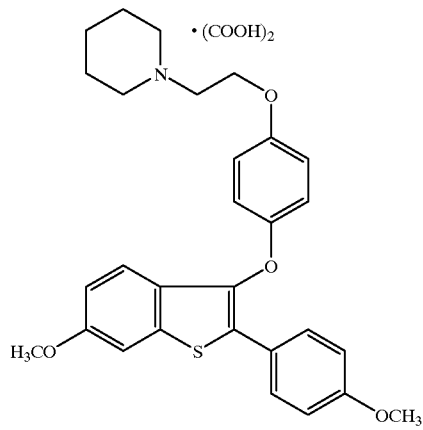

Step a: Preparation of [6-methoxy-2-(4-methoxy-phenyl)-3-bromo]benzo[b]thiophene

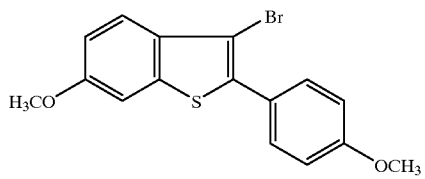

To a solution of [6-methoxy-2-(4-methoxyphenyl)]benzo-[b]thiophene (27.0 g, 100 mmol) in 1.10 L of chloroform at 60° C. was added bromine (15.98 g, 100 mmol) dropwise as a solution in 200 mL of chloroform. After the addition was complete, the reaction was cooled to room temperature, and the solvent removed in vacuo to provide 34.2 g (100%) of [6-methoxy-2-(4-methoxyphenyl)-3-bromo]benzo[b]thiophene as a white solid. mp 83–85° C. $^1$H NMR (DMSO-$d_6$) d 7.70–7.62 (m, 4H), 7.17 (dd, J=8.6, 2.0 Hz, 1H), 7.09 (d, J=8.4 Hz, 2H). FD mass spec: 349, 350. Anal. Calcd. for $C_{16}H_{13}O_2SBr$: C, 55.03; H, 3.75. Found: C, 54.79; H, 3.76.

Step b): Preparation of [6-methoxy-2-(4-methoxyphenyl)-3-(4-benzyloxy)phenoxy]benzo[b]thiophene

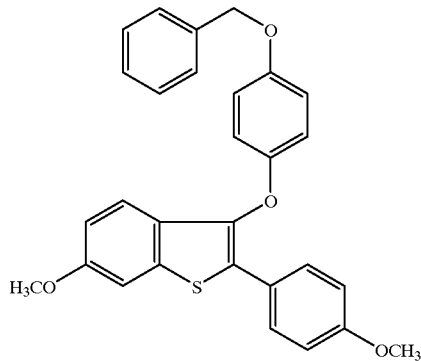

To a solution of [6-methoxy-2-(4-methoxyphenyl)-3-bromo]benzo[b]thiophene (34.00 g, 97.4 mmol) in 60 mL of collidine under $N_2$ was added 4-benzyloxyphenol (38.96 g, 194.8 mmol) and cuprous oxide (14.5 g, 97.4 mmol). The resultant mixture was heated to reflux for 48 hours. Upon cooling to room temperature, the mixture was dissolved in acetone (200 mL), and the inorganic solids were removed by filtration. The filtrate was concentrated in vacuo, and the residue dissolved in methylene chloride (500 mL). The methylene chloride solution was washed with 3N hydrochloric acid (3×300 mL), followed by 1N sodium hydroxide (3×300 mL). The organic layer was dried (sodium sulfate), and concentrated in vacuo. The residue was taken up in 100 mL of ethyl acetate whereupon a white solid formed that was collected by filtration [recovered [6-methoxy-2-(4-methoxyphenyl)]benzo-[b]thiophene (4.62 g, 17.11 mmol]. The filtrate was concentrated in vacuo, and then passed through a short pad of silica gel (methylene chloride as eluant) to remove baseline material. The filtrate was concentrated in vacuo, and the residue crystallized from hexanes/ethyl acetate to provide initially 7.19 g of [6-methoxy-2-(4-methoxyphenyl)-3-(4-benzyloxy) phenoxy]benzo[b]-thiophene as an off-white crystalline solid. The mother liquor was concentrated and chromatographed on silica gel (hexanes/ethyl acetate 80:20) to provide an additional 1.81 g of product. Total yield of [6-methoxy-2-(4-methoxyphenyl)-3-(4-benzyloxy) phenoxy]-benzo[b]thiophene was 9.00 g (24% based on recovered starting material). The basic extract was acidified to pH=4 with 5N hydrochloric acid, and the resultant precipitate collected by filtration and dried to give 13.3 g of recovered 4-benzyloxyphenol. mp 100–103° C. $^1$H NMR (CDCl$_3$): d 7.60 (d, J=8.8 Hz, 2H), 7.39–7.24 (m, 7H), 6.90–6.85 (m, 7H), 4.98 (s, 2H), 3.86 (s, 3H) 3.81 (s, 3H). FD mass spec: 468. Anal. Calcd. for $C_{29}H_{24}O_4S$: C, 74.34; H, 5.16. Found: C, 74.64; H, 5.29.

Step c): Preparation of [6-methoxy-2-(4-methoxyphenyl)-3-(4-hydroxy)phenoxy]benzo[b]thiophene

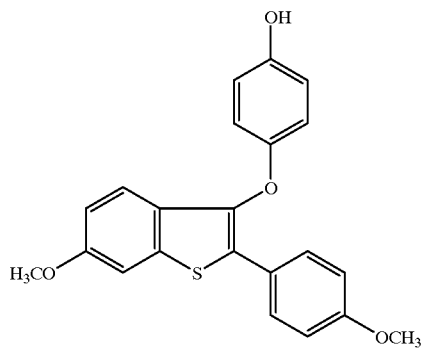

To a solution of [6-methoxy-2-(4-methoxyphenyl)-3-(4-benzyloxy)phenoxy]benzo[b]thiophene (1.50 g, 3.20 mmol) in 50 mL of ethyl acetate and 10 mL of 1% concentrated hydrochloric acid in ethanol was added 10% palladium-on-carbon (300 mg). The mixture was hydrogenated at 40 psi for 20 minutes, after which time the reaction was judged complete by thin layer chromatography. The mixture was passed through Celite to remove catalyst, and the filtrate concentrated in vacuo to a white solid. The crude product was passed through a pad of silica gel (chloroform as eluant). Concentration provided 1.10 g (91%) of [6-methoxy-2-(4-methoxyphenyl)-3-(4-hydroxy)phenoxy] benzo[b]-thiophene as a white solid. mp 123–126° C. $^1$H NMR (DMSO-$d_6$) d 9.10 (s, 1H), 7.59 (d, J=8.8 Hz, 2H), 7.52 (d, J=2.1 Hz, 1H), 7.14 (d, J=8.8 Hz, 1H), 6.95 (d, J=8.8 Hz, 2H), 6.89 (dd, J 8.8, 2.1 Hz, 1H), 6.72 (d, J=9.0 Hz, 2H), 6.63 (d, J=9.0 Hz, 2H), 3.78 (s, 3H), 3.72 (s, 3H). FD mass spec: 378. Anal. Calcd. for $C_{22}H_{18}O_4S$: C, 69.82; H, 4.79. Found: C, 70.06; H, 4.98.

Step d): Preparation of [6-methoxy-3-[4-[2-(1-piperidinyl) ethoxy]phenoxy]-2-(4-methoxyphenyl)]benzo[b]-thiophene oxalate salt To a solution of [6-methoxy-2-(4-methoxyphenyl)-3-(4-hydroxy)phenoxy]benzo[b]thiophene (1.12 g, 2.97 mmol) in 7 mL of anhydrous N,N-dimethylformamide under $N_2$ was added cesium carbonate (3.86 g, 11.88 mmol). After stirring for 10 minutes, 2-chloroethylpiperidine hydrochloride (1.10 g, 1.48 mmol) was added. The resultant mixture was stirred for 18 hours at ambient temperature. The reaction was the distributed between chloroform/water (100 mL each). The layers were separated and the aqueous extracted with chloroform (3×50 mL). The organic was combined and washed with water (2×100 mL). Drying of the organic (sodium sulfate) and concentration provided an oil that was chromatographed on silica gel (2% methanol/chloroform). The desired fractions were concentrated to an oil that was dissolved in 10 mL of ethyl acetate and treated with oxalic acid (311 mg, 3.4 mmol). After stirring for 10 minutes, a white precipitate formed and was collected by filtration and dried to provide 1.17 g (70%) overall of [6-methoxy-3-[4-[2-(1-piperidinyl)ethoxy]-phenoxy]-2-(4-methoxyphenyl)] benzo[b]thiophene as the oxalate salt. mp 197–200° C. (dec). $^1$H NMR (DMSO-$d_6$) d 7.60 (d, J=8.7 Hz, 2H), 7.55

(d, J=1.1 Hz, 1H), 7.14 (d, J=8.8 Hz, 1H), 7.06 (d, J=8.8 Hz, 2H), 6.91 (dd, J=8.8, 1.1 Hz, 1H), 6.87 (s, 4H), 4.19 (broad t, 2H), 3.78 (s, 3H), 3.72 (s, 3H), 3.32 (broad t, 2H), 3.12–3.06 (m, 4H), 1.69–1.47 (m, 4H), 1.44–1.38 (m, 2H). FD mass spec: 489. Anal. Calcd. for $C_{29}H_{31}NO_4S \cdot 0.88$ $HO_2CCO_2H$: C, 64.95; H, 5.80; N, 2.46. Found: C, 64.92; H, 5.77; N, 2.54.

EXAMPLE 2

Preparation of [6-methoxy-3-[4-[2-(1-piperidinyl)ethoxy]-phenoxyl-2-(4-methoxyphenyl)]benzo[b]thiophene hydrochloride salt

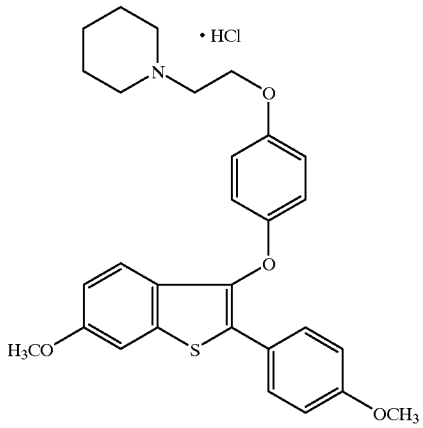

Treatment of the oxalate salt from Example 1 with aqueous base to produce the free base, followed by reaction with diethyl ether saturated with HCl yielded the title salt, mp 216–220° C. $^1$H NMR (DMSO-d$_6$) d 10.20 (bs, 1H), 7.64 (d, J=8.7 Hz, 2H), 7.59 (d, J=1.5 Hz, 1H), 7.18 (d, J=9.0 Hz, 1H), 7.00 (d, J=8.7 Hz, 1H), 6.96 (dd, J=9.0, 1.5 Hz, 1H), 6.92 (q, $J_{AB}$=9.0 Hz, 4H), 4.31 (m, 2H), 3.83 (s, 3H), 3.77 (s, 3H), 3.43 (m, 4H), 2.97 (m, 2H), 1.77 (m, 5H), 1.37 (m, 1H). FD mass spec: 489. Anal. Calcd. for $C_{29}H_{31}NO_4S \cdot 1.0$ HCl: C, 66.21; H, 6.13; N, 2.66. Found: C, 66.,46; H, 6.16; N, 2.74.

EXAMPLE 3

Preparation of (6-Methoxy-3-[4-[2-(1-pyrolodinyl)ethoxy]-phenoxy]-2-(4-methoxyphenyl)]benzo[b]thiophene

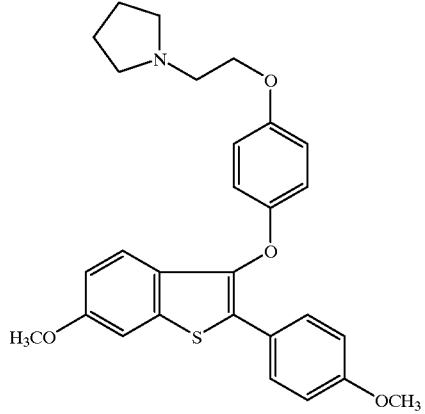

The title compound was prepared in the same manner as the compound of Example 1, mp 95–98° C. $^1$H NMR (DMSO-d$_6$) d 7.64 (d, J=9.0 Hz, 2H), 7.58 (d, J=2.0 Hz, 1H), 7.18 (d, J=9.0 Hz, 1H), 7.00 (d, J=9.0 Hz, 2H), 6.94 (dd, J=9.0, 2.0 Hz, 1H), 6.86 (s, 4H), 3.97 (t, J=6.0 Hz, 2H), 3.83 (s, 3H), 3.76 (s, 3H), 2.73 (t, J=6.0 Hz, 2H), 2.51 (m, 4H), 1.66 (m, 4H). FD mass spec: 477. Anal. Calcd. for $C_{28}H_{29}NO_4S$: C, 70.71; H, 6.15; N, 2.99. Found: C, 70.59; H, 6.15; N, 3.01.

EXAMPLE 4

Preparation of [6-Methoxy-3-[4-[2-(1-hexamethyleneimino)ethoxy]phenoxy]-2-(4-methoxyphenyl)]benzo[b]thiophene hydrochloride

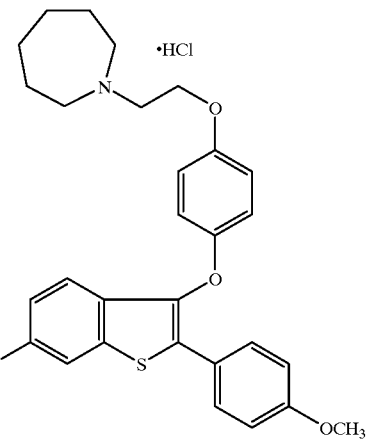

The title compound was prepared in the same manner as the compound of Example 1, mp 189–192° C. $^1$H NMR (DMSO-d$_6$) d 10.55 (bs, 1H), 7.64 (d, J=9.0 Hz, 2H), 7.58 (d, J=2.0 Hz, 1H), 7.19 (d, J=9.0 Hz, 1H), 7.00 (d, J=9.0 Hz, 2H), 6.95 (dd, J=9.0, 2.0 Hz, H), 6.86 (s, 4H), 3.94 (t, J=6.0 Hz, 2H), 3.83 (s, 3H), 3.76 (s, 3H), 2.80 (t, J=6.0 Hz, 2H), 2.66 (m, 4H), 1.53 (m, 8H). Anal. Calcd. for $C_{30}H_{33}NO_4S \cdot 1.0$ HCl: C, 66.71; H, 6.35; N, 2.59. Found: C, 66.43; H, 6.46; N, 2.84.

EXAMPLE 5

Preparation of [6-Methoxy-3-[4-[2-(1-N,N-diethylamino)ethoxy]phenoxy]-2-(4-methoxyphenyl)]benzo[b]thiophene hydrochloride

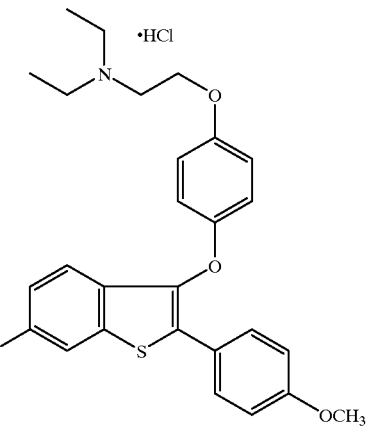

The title compound was prepared in the same manner as the compound of Example 1, mp 196–198° C. $^1$H NMR (DMSO-d$_6$) d 10.48 (bs, 1H), 7.64 (d, J=9.0 Hz, 2H), 7.59 (d, J=2.0 Hz, 1H), 7.19 (d, J=9.0 Hz, 1H), 7.00 (d, J=9.0 Hz, 2H), 6.97 (dd, J=9.0, 2.0 Hz, 1H), 6.87 (q, $J_{AB}$=9.0 Hz, 4H), 4.25 (m, 2H), 3.83 (s, 3H), 3.77 (s, 3H), 3.54 (m, 2H), 3.09 (m, 4H), 2.00 (m, 3H), 1.88 (m, 3H). Anal. Calcd. for $C_{28}H_{31}NO_4S \cdot 1.5$ HCl: C, 63.18; H, 6.15; N, 2.63. Found: C, 63.46; H, 5.79; N, 2.85.

EXAMPLE 6
Preparation of [6-Methoxy-3-[4-[2-(morpholino)ethoxy]-phenoxy]-2-(4-methoxyphenyl)]benzo[b]thiophene hydrochloride

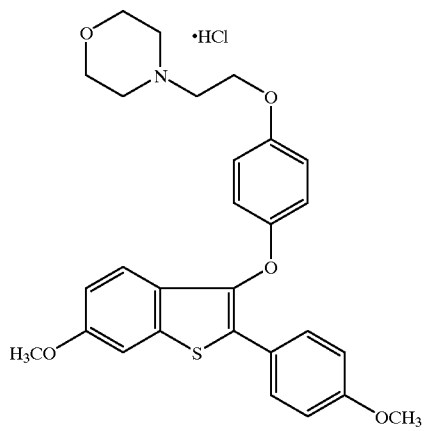

The title compound was prepared in the same manner as the compound of Example 1, mp 208–211° C. $^1$H NMR (DMSO-$d_6$) d 10.6 (bs, 1H), 7.63 (d, J=9.0 Hz, 2H), 7.60 (d, J=2.0 Hz, 1H), 7.20 (J=9.0 Hz, 1H), 7.00 (d, J=9.0 Hz, 2H), 6.97 (dd, J=9.0, 2.0 Hz, 1H), 6.91 (q, $J_{AB}$=9.0 Hz, 4H), 4.29 (m, 2H), 4.08–3.91 (m, 4H), 3.82 (s, 3H), 3.77 (s, 3H), 3.59–3.42 (m, 4H), 3.21–3.10 (m, 2H). Anal. Calcd. for $C_{28}H_{29}NO_5S \cdot 1.0$ HCl: C, 63.09; H, 5.73; N, 2.65. Found: C, 63.39; H, 5.80; N, 2.40.

EXAMPLE 7
Preparation of [6-Hydroxy-3-[4-[2-(1-piperidinyl)ethoxy]-phenoxy]-2-(4-hydroxyphenyl)]benzo[b]thiophene

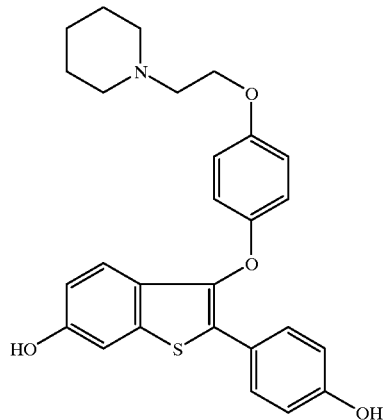

[6-methoxy-3-[4-[2-(1-piperidinyl)ethoxy]phenoxy]-2-(4-methoxyphenyl)]benzo[b]thiophene hydrochloride (10.00 g, 19.05 mmol) was dissolved in 500 mL of anhydrous methylene chloride and cooled to 8° C. To this solution was added boron tribromide (7.20 mL, 76.20 mmol). The resultant mixture was stirred at 8° C. for 2.5 hours. The reaction was quenched by pouring into a stirring solution of saturated sodium bicarbonate (1 L), cooled to 0° C. The methylene chloride layer was separated, and the remaining solids were dissolved in methanol/ethyl acetate. The aqueous layer was then extracted with 5% methanol/ethyl acetate (3×500 mL). All of the organic extracts (ethyl acetate and methylene chloride) were combined and dried (sodium sulfate). Concentration in vacuo provided a tan solid that was chromatographed (silicon dioxide, 1–7% methanol/chloroform) to provide 7.13 g (81%) of [6-hydroxy-3-[4-[2-(1-piperidinyl) ethoxy]phenoxy]-2-(4-hydroxyphenyl)]benzo[b]-thiophene as a white solid. mp 93° C. $^1$H NMR (DMSO-$d_6$) d 9.73 (bs, 1H), 9.68 (bs, 1H), 7.45 (d, J=8.6 Hz, 2H), 7.21 (d, J=1.8 Hz, 1H), 7.04 (d, J=8.6 Hz, 1H), 6.84 (dd, J=8.6, 1.8 Hz, 1H (masked)), 6.81 (s, 4H), 6.75 (d, J=8.6 Hz, 2H), 3.92 (t, J=5.8 Hz, 2H), 2.56 (t, J=5.8 Hz, 2H), 2.36 (m. 4H), 1.43 (m, 4H), 1.32 (m, 2H). FD mass spec: 462. Anal. Calcd. for $C_{27}H_{27}NO_4S$: C, 70.20; H, 5.90; N, 3.03. Found: C, 69.96; H, 5.90; N, 3.14.

EXAMPLE 8
Preparation of [6-Hydroxy-3-[4-[2-(1-piperidinyl)ethoxy]-phenoxy]-2-(4-hydroxyphenyl)]benzo[b]thiophene oxalate salt

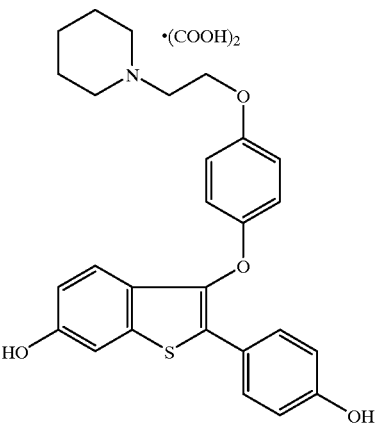

The title compound was prepared in 80% yield from the free base, mp 246–249° C. (dec). $^1$H NMR (DMSO-$d_6$) d 7.45 (d, J=8.6 Hz, 2H), 7.22 (d, J=1.8 Hz, 1H), 7.05 (d, J=8.6 Hz, 1H), 6.87 (dd, J=8.6, 1.8 Hz, 1H (masked)), 6.84 (s, 4H), 6.75 (d, J=8.6 Hz, 2H), 4.08 (bt, 2H), 3.01 (bt, 2H), 2.79 (m, 4H), 1.56 (m, 4H), 1.40 (m, 2H). FD mass spec 462. Anal. Calcd. for $C_{27}H_{27}NO_4S \cdot 0.75$ $HO_2CCO_2H$: C, 64.63; H, 5.42; N, 2.64. Found: C, 64.61; H, 5.55; N, 2.62.

EXAMPLE 9
Preparation of [6-Hydroxy-3-[4-[2-(1-piperidinyl)ethoxy]-phenoxy]-2-(4-hydroxyphenyl)]benzo[b]thiophene hydrochloride

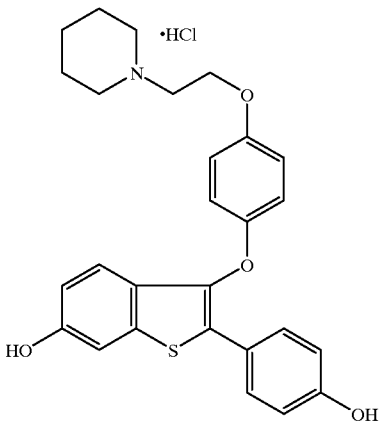

The title compound was prepared in 91% yield by treatment of the corresponding free base with HCl saturated diethyl ether, mp 158–165° C. $^1$H NMR (DMSO-d$_6$) d 9.79 (s, 1H), 9.74 (s, 1H), 7.40 (d, J=8.6 Hz, 2H), 7.23 (d, J=2.0 Hz, 1H), 7.04 (d, J=8.6 Hz, 1H), 6.86 (q, J$_{AB}$=9.3 Hz, 4H), 6.76 (dd, J=8.6, 2.0 Hz, 1), 6.74 (d, J=8.6 Hz, 2H), 4.26 (bt, 2H), 3.37 (m, 4H), 2.91 (m, 2H), 1.72 (m, 5 H), 1.25 (m, 1H). FD mass spec 461. Anal. Calcd. for C$_{27}$H$_{27}$NO$_4$S.1.0 HCl: C, 65.11; H. 5.67; N, 2.81. Found: C, 64.84; H, 5.64; N, 2.91.

EXAMPLE 10

Preparation of [6-Hydroxy-3-[4-[2-(1-pyrolidinyl)ethoxy]-phenoxy]-2-(4-hydroxyphenyl)]benzo[b]thiophene

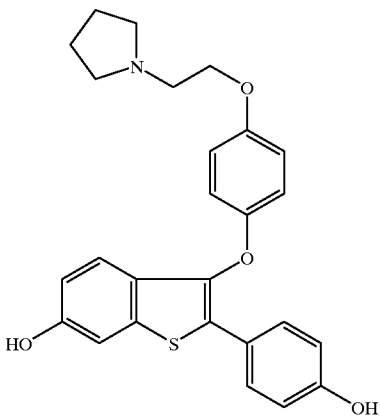

The title compound was prepared from the product of Example 3 in a manner similar to that employed in Example 7 above; mp 99–113° C. $^1$H NMR (DMSO-d$_6$) d 9.75 (s, 1H), 9.71 (s, 1H), 7.50 (d, J 9.0 Hz, 2H), 7.25 (d, J=2.0 Hz, 1H), 7.09 (d, J=9.0 Hz, 1H), 6.85 (s, 1H), 6.80 (dd, J=9.0, 2.0 Hz, 1H), 6.79 (d, J=9.0 Hz, 2H), 3.93 (m, 2H), 2.73 (m, 2H), 2.53 (m, 4H), 0.96 (t, J=7.0 Hz, 4H). Anal. Calcd. for C$_{26}$H$_{25}$NO$_4$S.0.5 H$_2$O: C, 68.40; H, 5.74; N, 3.07. Found: C, 68.52; H, 6.00; N, 3.34.

EXAMPLE 11

Preparation of [6-Hydroxy-3-[4-[2-(1-hexamethyleneimino)ethoxy]phenoxy]-2-(4-hydroxyphenyl)]benzo[b]thiophene The title compound was prepared from the product of Example 4 in a manner similar to that employed in Example 7 above; mp 125–130° C. $^1$H NMR (DMSO-d$_6$) d 9.75 (s, 1H), 9.71 (s, 1H), 7.50 (d, J=9.0 Hz, 2H), 7.26 (d, J=2.0 Hz, 1H), 7.09 (d, J=9.0 Hz, 1H), 6.85 (s, 3H), 6.80 (dd, J=9.0, 2.0 Hz, 1H), 6.79 (d, J=9.0 Hz), 3.94 (t, J=6.0 Hz, 2H), 2.80 (t, J=6.0 Hz, 2H), 2.66 (m, 4H), 1.53 (m, 8H). Anal. Calcd. for C$_{28}$H$_{29}$NO$_4$S: C, 70.71; H, 6.15; N, 2.94. Found: C, 70.67; H, 6.31; N, 2.93.

EXAMPLE 12

Preparation of [6-Hydroxy-3-[4-[2-(1-N,N-diethylamino)ethoxy]phenoxy]-2-(4-hydroxyphenyl)]benzo[b]thiophene

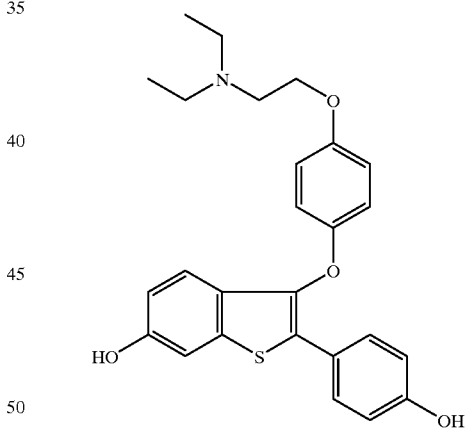

The title compound was prepared from the product of Example 5 in a manner similar to that employed in Example 7 above; mp 137–141° C. $^1$H NMR (DMSO-d$_6$) d 9.75 (s, 1H), 9.71 (s, 1H), 7.49 (d, J=9.0 Hz, 1H), 7.25 (d, j=2.0 Hz, 1H), 7.09 (d, J=9.0 Hz, 1H), 6.85 (s, 4H), 6.80 (dd, J=9.0, 2.0 Hz, 1H), 6.79 (d, J=9.0 Hz, 2H), 3.95 (t, J=6.0 Hz, 2H), 2.74 (t, J=6.0 Hz, 2H), 2.51 (m, 4H), 1.66 (m, 6H). Anal. Calcd. for C$_{26}$H$_{27}$NO$_4$S: C, 69.46; H, 6.05; N, 3.12. Found: C, 69.76; H, 5.85; N, 3.40.

EXAMPLE 13

Preparation of [6-Hydroxy-3-[4-[2-(morpholino)ethoxy]-phenoxy]-2-(4-hydroxyphenyl)]benzo[b]thiophene hydrochloride

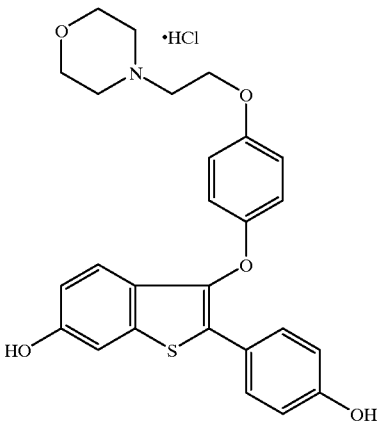

The title compound was prepared from the product of Example 6 in a manner similar to that employed in Example 7 above; mp 157–162° C. $^1$H NMR (DMSO-$d_6$) d 10.60 (bs, 1H), 9.80 (s, 1H), 9.75 (s, 1H), 7.50 (d, J=9.0 Hz, 2H), 7.28 (d, J=2.0 Hz, 1H), 7.10 (d, J=9.0 Hz, 1H), 6.92 (q, $J_{AB}$=9.0 Hz, 4H), 6.81 (dd, J=9.0, 2.0 Hz, 1H), 6.80 (d, J=9.0 Hz, 2H), 4.30 (m, 2H), 3.95 (m, 2H), 3.75 (m, 2H), 3.51 (m, 4H), 3.18 (m, 2H). Anal. Calcd. for $C_{26}H_{25}NO_5S \cdot HCl$: C, 62.46; H, 5.24; N, 2.80. Found: C, 69.69; H, 5.43; N, 2.92.

EXAMPLE 14

Preparation of [6-Hydroxy-3-[4-[2-(1-piperidinyl)-ethoxy]-phenoxy]-2-(4-methoxyphenyl)]benzo[b]thiophene

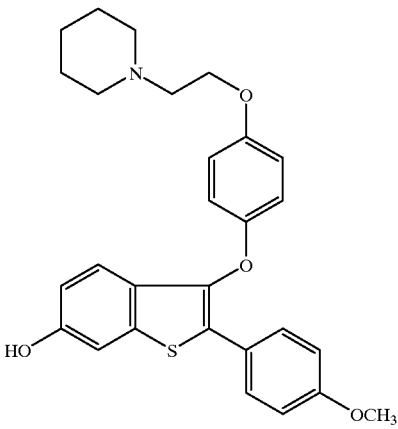

Step a): Preparation of 6-Methoxybenzo[b]thiophene-2-boronic acid

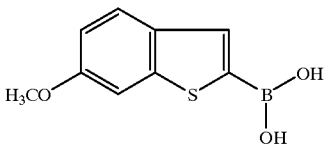

To a solution of 6-methoxybenzo[b]thiophene (18.13 g, 0.111 mol) in 150 mL of anhydrous tetrahydrofuran (THF) at −60° C. was added n-butyllithium (76.2 mL, 0.122 mol, 1.6 M solution in hexanes), dropwise via syringe. After stirring for 30 minutes, triisopropyl borate (28.2 mL, 0.122 mol) was introduced via syringe. The resulting mixture was allowed to gradually warm to 0° C. and then distributed between 1N hydrochloric acid and ethyl acetate (300 mL each). The layers were separated, and the organic layer was dried over sodium sulfate. Concentration in vacuo produced a white solid that was triturated from ethyl ether hexanes. Filtration provided 16.4 g (71%) of 6-methoxybenzo[b]thiophene-2-boronic acid as a white solid. mp 200° C. (dec). $^1$H NMR (DMSO-$d_6$) d 7.83 (s, 1H), 7.78 (d, J=8.6 Hz, 1H), 7.51 (d, J 2.0 Hz, 1H), 6.97 (dd, J=8.6, 2.0 Hz, 1H), 3.82 (s, 3H). FD mass spec: 208.

Step b): Preparation of [6-Methoxy-2-(4-methanesulfonyloxyphenyl)]benzo[b]thiophene

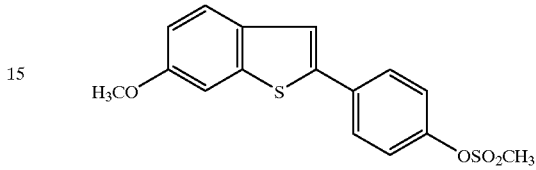

To a solution of 6-methoxybenzo[b]thiophene-2-boronic acid (3.00 g, 14.4 mnol) in 100 mL of toluene was added 4-(methanesulfonyloxy)phenylbromide (3.98 g, 15.8 mmol) followed by 16 mL of 2.0 N sodium carbonate solution. After stirring for 10 minutes, tetrakistriphenylphosphine-palladium (0.60 g, 0.52 mmol) was added, and the resulting mixture was heated to reflux for 5 hours. The reaction mixture was then allowed to cool to ambient temperature whereupon the product precipitated from the organic phase. The aqueous phase was removed and the organic layer was concentrated in vacuo to a solid. Trituration from ethyl ether yielded a solid that was filtered and dried in vacuo to provide 3.70 g (77%) of [6-methoxy-2-(4-methanesulfonyloxy-phenyl)]benzo[b]thiophene as a tan solid. mp 197–201° C. $^1$H NMR (DMSO-$d_6$) d 7.82–7.77 (m, 3H), 7.71 (d, J=8.8 Hz, 1H), 7.54 (d, J=2.3 Hz, 1H), 7.40 (d, J=8.7 Hz, 2H), 6.98 (dd, J=8.7, 1.5 Hz, 1H), 3.80 (s, 3H), 3.39 (s, 3H). FD mass spec 334. Anal. Calcd. for $C_{16}H_4O_4S_2$: C, 57.46; H, 4.21. Found: C, 57.76; H, 4.21.

Step c): Preparation of [6-Hydroxy-2-(4-methanesulfonyloxyphenyl)]benzo[b]thiophene

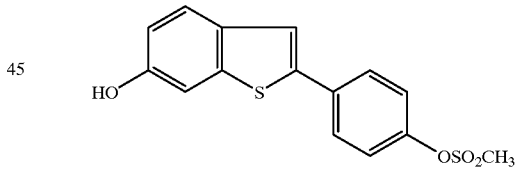

To a solution of [6-methoxy-2-(4-methanesulfonyloxyphenyl)]benzo[b]thiophene (9.50 g, 28.40 mmol) in anhydrous methylene chloride (200 mL) at room under nitrogen gas was added boron tribromide (14.20 g, 5.36 mL, 56.8 mmol). The resulting mixture was stirred at ambient temperature for 3 hours. The reaction was quenched by slowly pouring into excess ice water. After vigorously stirring for 30 minutes, the white precipitate was collected by filtration, washed several times with water, and then dried in vacuo to provide 8.92 g (98%) of [6-hydroxy-2-(4-methanesulfonyloxyphenyl)]benzo[b]thiophene as a white solid. mp 239–243° C. $^1$H NMR (DMSO-$d_6$) d 9.70 (s, 1H), 7.76 (d, J=8.7 Hz, 2H), 7.72 (s, 1H), 7.62 (d, J=8.7 Hz, 1H), 7.38 (d, J=8.7 Hz, 2H), 7.24 (d, J=1.7 Hz, 1H), 6.86 (dd, J=8.7, 1.7 Hz, 1H), 3.38 (s, 3H). FD mass spec 320. Anal. Calcd. for $C_{15}H_{12}O_4S_2$: C, 56.23; H, 3.77. Found: C, 56.49; H, 3.68.

Step d): Preparation of [6-Benzyloxy-2-(4-methanesulfonyloxyphenyl)]benzo[b]thiophene

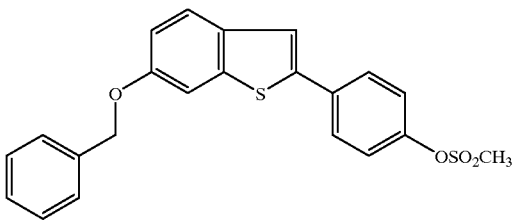

To a solution of [6-hydroxy-2-(4-methanesulfonyloxyphenyl)]benzo[b]thiophene (3.20 g, 10.0 mmol) in 75 mL of anhydrous DMF was added $Cs_2CO_3$ (5.75 g, 17.7 mmol) followed by benzylchloride (1.72 mL, 11.0 mmol). The resulting mixture was stirred vigorously for 24 hours. The solvent was removed in vacuo, and the solid residue was suspended in 200 mL of water. The white precipitate was collected by filtration and washed several times with water. Upon drying in vacuo, the crude product was suspended in 1:1 hexanes:ethyl ether. The solid was collected to provide 3.72 g (91%) of [6-benzyloxy-2-(4-methanesulfonyloxyphenyl)]benzo[b]thiophene as a white solid. mp 198–202° C. $^1$H NMR (DMSO-$d_6$) d 7.81–7.78 (m, 3H), 7.72 (d, J=8.7 Hz, 1H), 7.64 (d, J=2.2 Hz, 1H), 7.47–7.30 (m, 7H), 5.15 (s, 2H), 3.39 (s, 3H). FD mass spec 410.

Step e): Preparation of [6-Benzyloxy-2-(4-hydroxyphenyl)]-benzo[b]thiophene

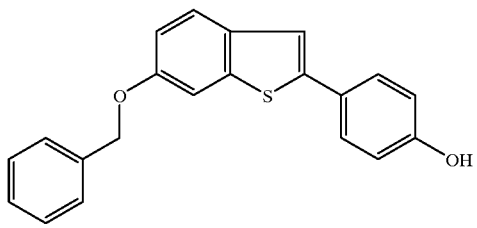

To a solution of [6-benzyloxy-2-(4-methanesulfonyloxyphenyl)]benzo[b]thiophene (12.50 g, 30.50 mmol) in 300 mL of anhydrous THF under nitrogen gas at ambient temperature was added lithium aluminum hydride (2.32 g, 61.0 mmol) in small portions. The mixture was then stirred at ambient temperature for 3 hours and then quenched by carefully pouring the mixture into an excess of cold 1.0 N hydrochloric acid. The aqueous phase was extracted with ethyl acetate. The organic was then washed several times with water and then dried (sodium sulfate) and concentrated in vacuo to a solid. Chromatography (silicon dioxide, chloroform) provided 8.75 g (87%) of [6-benzyloxy-2-(4-hydroxyphenyl)]benzo[b]thiophene as a white solid. mp 212–216° C. $^1$H NMR (DMSO-$d_6$) d 9.70 (s, 1H), 7.63 (d, J=8.7 Hz, 1H), 7.56 (d, J=2.2 Hz, 1H), 7.51–7.30 (m, 8H), 7.00 (dd, J=8.7, 2.2 Hz, 1H), 6.80 (d, J=8.6 Hz, 2H), 5.13 (s, 2H). FD mass spec 331. Anal. Calcd. for $C_{21}H_6O_2S$: C, 75.88; H, 4.85. Found: C, 75.64; H, 4.85.

Step f): Preparation of [6-Benzyloxy-2-(4-methoxyphenyl)]-benzo[b]thiophene

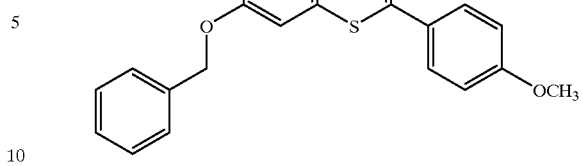

To a solution of [6-benzyloxy-2-(4-hydroxyphenyl)]benzo[b]thiophene (8.50 g, 26.40 mmol) in 200 mL of anhydrous DMF under nitrogen gas at ambient temperature was added sodium hydride (1.66 g, 41.5 mmol) in small portions. Once gas evolution had ceased, iodomethane (3.25 mL, 52.18 mmol) was added dropwise. The reaction was stirred for 3 hours at ambient temperature. The solvent was then removed in vacuo, and the residue distributed between water/ethyl acetate. The layers were separated, and the organic phase was washed several times with water. The organic layer was then dried (sodium sulfate) and concentrated in vacuo to provide 9.00 g (98%) of [6-benzyloxy-2-(4-methoxyphenyl)]benzo[b]thiophene as a white solid. mp 180–185° C. $^1$H NMR (DMSO-$d_6$) d 7.67–7.58 (m, 5H), 7.46–7.29 (m, 5H), 7.02 (dd, J=8.8, 2.2 Hz, 1H), 6.98 (d, J=8.7 Hz, 2H), 5.13 (s, 2H), 3.76 (s, 3H). FD mass spec 346. Anal. Calcd. for $C_{22}H_{18}O_2S$: C, 76.27; H, 5.24. Found: C, 76.54; H, 5.43.

Step g): Preparation of [6-Benzyloxy-2-(4-methoxyphenyl)-3-bromo]benzo[b]thiophene

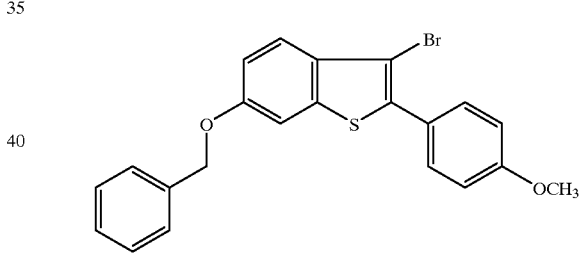

[6-Benzyloxy-2-(4-methoxyphenyl)]benzo[b]thiophene (10.0 g, 28.9 mmol) was placed in 200 mL of chloroform along with 10.0 g of solid sodium bicarbonate at ambient temperature. To this suspension was added bromine (1.50 mL, 29.1 mmol) dropwise over 30 minutes as a solution in 100 mL of chloroform. Upon completion of the addition, water (200 mL) was added and the layers were separated. The organic phase was dried (sodium sulfate) and concentrated in vacuo to a white solid. Crystallization from methylene chloride/methanol provided 10.50 g (85%) of [6-benzyloxy-2-(4-methoxyphenyl)-3-bromo]benzo-[b]thiophene as a white solid. mp 146–150° C. $^1$H NMR (DMSO-$d_6$) d 7.70 (d, J=2.2 Hz, 1H), 7.65–7.60 (m, 3H), 7.47–7.30 (m, 5H), 7.19 (dd, J=8.8, 2.2 Hz, 1H), 7.06 (d, J=8.7 Hz, 2H), 5.17 (s, 2H), 3.78 (s, 3H). FD mass spec 346. Anal. Calcd. for $C_{22}H_{17}O_2SBr$: C, 62.13; H, 4.03. Found: C, 61.87; H, 4.00.

Step h): Preparation of [6-Benzyloxy-2-(4-methoxyphenyl)-3-bromo]benzo[b]thiophene-(S-oxide)

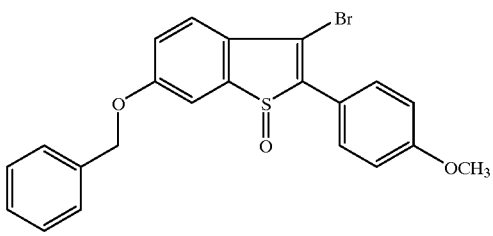

The title compound was prepared by oxidation of the product from step g) with 1.5 equivalents of hydrogen peroxide in a mixture of trifluoroacetic acid in methylene chloride. The product was isolated as a yellow solid by crystallization from ethyl acetate. mp 202–205° C. $^1$H NMR (DMSO-d$_6$) d 7.80 (d, J=2.2 Hz, 1H), 7.68 (d, J=8.7 Hz, 2H), 7.55(d, J=8.4 Hz, 1H) 7.47–7.32 (m, 6H), 7.10 (d, J=8.7 Hz, 2H), 5.23 (s, 2H), 3.80 (s, 3H). FD mass spec 441. Anal. Calcd. for $C_{22}H_{17}O_3SBr$: C, 59.87; H, 3.88. Found: C, 59.59; H, 3.78.

Step i): Preparation of [6-Benzyloxy-3-[4-[2-(1-piperidinyl)ethoxy]phenoxy]-2-(4-methoxyphenyl)]-benzo[b]thiophene-(S-oxide)

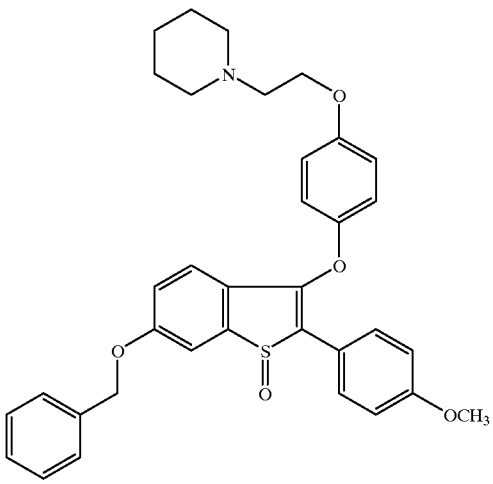

Reaction of the product of step i) above with 4-(2-piperidinoethoxy)phenol in base yielded the title compound as a yellow oil. $^1$H NMR (DMSO-d$_6$) d 7.76 (d, J=2.2 Hz, 1H), 7.62 (d, J=8.8 Hz, 2H), 7.44–7.30 (m, 5H), 7.12 (dd, J=8.6, 2.2 Hz, 1H), 7.03–6.93 (m, 5H), 6.85 (d, J=8.8 Hz, 2H), 5.18 (s, 2H), 3.94 (bt, J=5.8 Hz, 2H), 3.73 (s, 3H), 2.56 (bt, J=5.8 Hz, 2H), 2.37–2.34 (m, 4H), 1.45–1.32 (m, 6H). FD mass spec 592. Anal. Calcd. for $C_{35}H_{35}NO_5S$: C, 72.26; H, 6.06; N, 2.41. Found: C, 72.19; H, 5.99; N, 2.11.

Step j): Preparation of [6-Benzyloxy-3-[4-[2-(1-piperidinyl)ethoxy]phenoxy]-2-(4-methoxyphenyl)]-benzo[b]thiophene

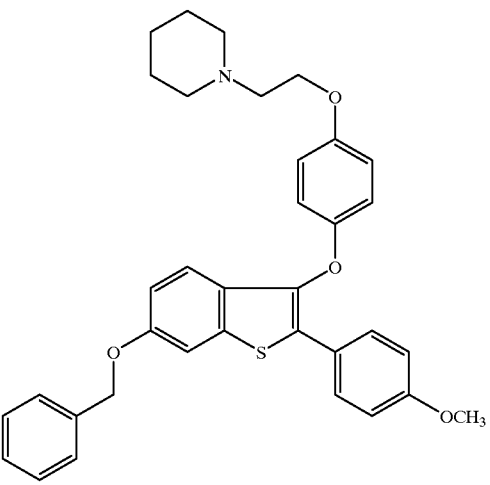

Reduction of the product of step i) above yielded the title compound, isolated in 95% overall yield. Purification by chromatography (SiO$_2$, 1–5% methanol/chloroform) provided an off-white solid, mp 105–108° C. $^1$H NMR (DMSO-d$_6$) d 7.62 (d, J=2.2 Hz, 1H), 7.59 (d, J=8.8 Hz, 2H), 7.45–7.30 (m, 5H), 7.15 (dd, J=8.6 Hz, 1H), 7.00–6.94 (m, 3H), 6.82 (s, 4H), 5.13 (s, 2H), 3.92 (bt, J=5.8 Hz, 2H), 3.72 (s, 3H), 2.55 (bt, J=5.8 Hz, 2H), 2.37–2.34 (m, 4H), 1.44–1.31 (m, 4H). FD mass spec 565. Anal. Calcd. for $C_{35}H_{35}NO_4S$: C, 74.31; H, 6.24; N, 2.48. Found: C, 74.35; H, 6.07; N, 2.76.

Step k): Preparation of [6-Hydroxy-3-[4-[2-(1-piperidinyl)ethoxy]phenoxy]-2-(4-methoxyphenyl)]benzo[b]-thiophene

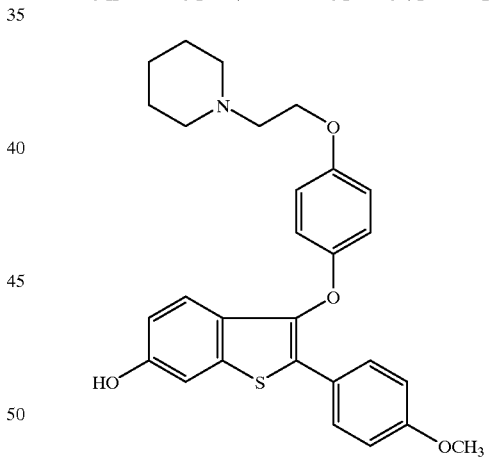

To a solution of [6-benzyloxy-3-[4-[2-(1-piperidinyl)ethoxy]phenoxy]-2-(4-methoxyphenyl)]benzo[b]thiophene (8.50 In g, 15.0 mmol) in 300 mL of 5:1 ethanol/ethyl acetate was added palladium black (1.50 g), ammonium formate (3.50 g, 55.6 mmol), and 30 mL of water. The resulting mixture was c heated to reflux and monitored by TLC. After approximately 3 hours, the reaction was judged complete and the solution was cooled to ambient temperature. The reaction was filtered through a pad of Celite to remove catalyst, and the filtrate was concentrated in vacuo to a solid. The concentrate was distributed between saturated sodium bicarbonate solution and 5% ethanol/ethyl acetate. The layers were separated, and the organic phase was dried (sodium sulfate) and concentrated in vacuo. The crude product was chromatographed (silicon dioxide, 1–5% methanol/chloroform) to provide 6.50 g (91%) of [6-hydroxy-3-[4-[2-(1-piperidinyl) ethoxy]phenoxy]-2-(4-methoxyphenyl)]benzo[b]thiophene as foam that converted to solid upon trituration with hexanes. mp 174–176° C. $^1$H NMR (DMSO-d$_6$) d 9.77 (s, 1H), 7.56 (d, J=8.8 Hz, 2H), 7.23 (d, J=2.0 Hz, 1H), 7.07 (d, J=8.6 Hz, 1H), 6.93 (d, J=8.8 Hz, 2H), 6.81 (s, 4H), 6.76 (dd, J=8.6, 2.0 Hz, 1H), 3.91 (bt, J=5.9 Hz, 2H), 3.71 (s, 3H), 2.55 (bt, J=5.9 Hz, 2H), 2.38–2.33 (m, 4H), 1.46–1.28 (m, 6H). FD mass spec 475. Anal. Calcd. for C$_{28}$H$_{29}$NO$_4$S: C, 70.71; H, 6.15; N, 2.94. Found: C, 70.46; H, 5.93; N, 2.71.

EXAMPLE 15

Preparation of [6-Hydroxy-3-[4-[2-(1-piperidinyl)ethoxy]-phenoxy]-2-(4-methoxyphenyl)]benzo[b]thiophene hydrochloride salt

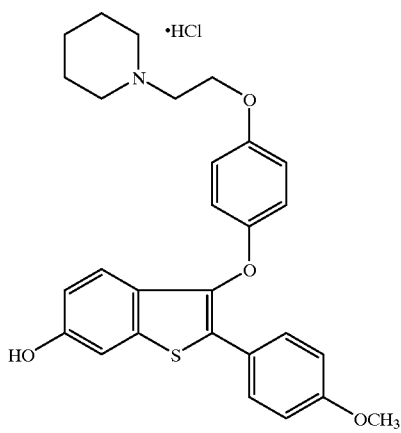

The product of Example 14 was converted to the corresponding hydrochloride salt in 85% yield by treatment with a mixture of HCl saturated diethyl ether in ethyl acetate followed by crystallization from ethanol/ethyl acetate; mp 156–160° C. $^1$H NMR (DMSO-d$_6$) d 10.28 (bs, 1H), 9.85 (s, 1H), 7.56 (d, J=8.8 Hz, 2H), 7.25 (d, J=2.0 Hz, 1H), 7.06 (d, J=8.7 Hz, 1H), 6.93 (d, J=8.8 Hz, 2H), 6.87 (q, J$_{AB}$=9.3 Hz, 4H), 4.27 (bt, J=5.9 Hz, 2H), 3.71 (s, 3H), 3.44–3.31 (m, 4H), 2.98–2.88 (m, 2H), 1.74–1.60 (m, 5H), 1.36–1.29 (m, 1H) FD mass spec 475. Anal. Calcd. for C$_{28}$H$_{29}$NO$_4$S.1.0 HCl: C, 65.68; H, 5.90; N, 2.73. Found: C, 65.98; H, 6.11; N, 2.64.

EXAMPLE 16

Preparation of [6-methoxy-3-[4-[2-(1-piperidinyl)ethoxy]phenoxy]-2-(4-hydroxyphenyl)]benzo[b]thiophene

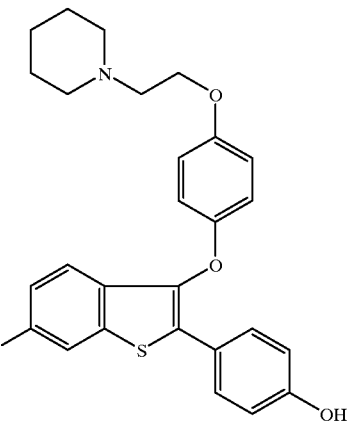

Step a): Preparation of [6-methoxy-2-(4-benzyloxyphenyl)]-benzo[b]thiophene

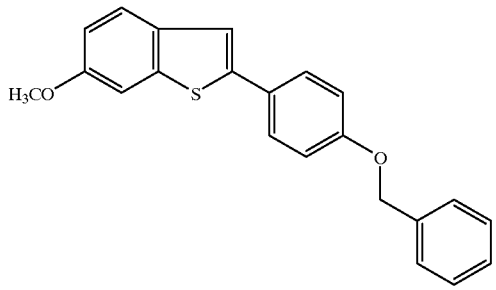

Following the general procedures of steps a) through g) of Example 14, the title compound was obtained in 73% yield, mp 217–221° C. $^1$H NMR (DMSO-d$_6$) d 7.63–7.60 (m, 3H), 7.59–7.26 (m, 7H), 7.02 (d, J=8.7 Hz, 2H), 6.96 (dd, J=8.8, 2.2 Hz, 1H), 5.11 (s, 2H), 3.88 (s, 3H). FD mass spec 346. Anal. Calcd. for C$_{22}$H$_{18}$O$_2$S: C, 76.27; H, 5.24. Found: C, 76.00; H, 5.25.

Step b): [6-methoxy-2-(4-benzyloxyphenyl)-3-bromo]benzo-[b]thiophene

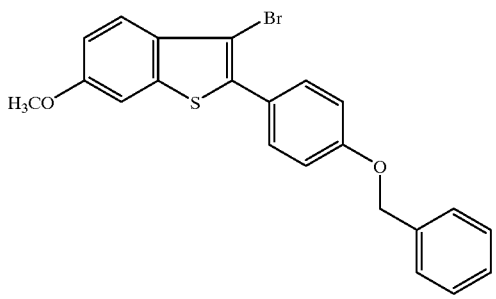

The title compound was obtained in 91% yield, mp 125–127° C. $^1$H NMR (DMSO-d$_6$) d 7.64–7.61 (m, 4H), 7.46–7.31 (m, 5H), 7.15–7.09 (m, 3H), 5.15 (s, 2H), 3.82 (s, 3H). FD mass spec 346. Anal. Calcd. for C$_{22}$H$_{17}$O$_2$SBr: C, 62.13; H, 4.03. Found: C, 62.33; H, 3.93.

Step c): [6-Methoxy-2-(4-benzyloxyphenyl)-3-bromo]benzo[b]-thiophene-(S-oxide)

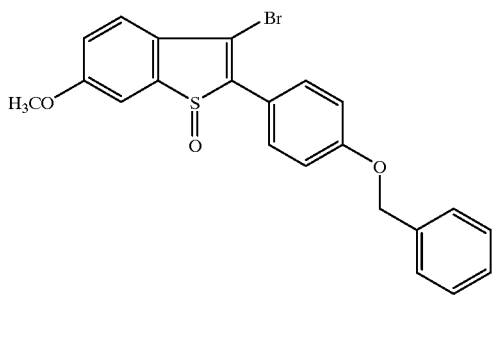

The title compound was isolated as a yellow solid by chromatography (SiO$_2$, CHCl$_3$). mp 119–123° C. $^1$H NMR (DMSO-d$_6$) d 7.73 (d, J=2.2 Hz, 1H), 7.68 (d, J=8.8 Hz, 2H), 7.55 (d, J=8.5 Hz, 1H) 7.46–7.31 (m, 5), 7.26 (dd, J=8.5, 2.2 Hz, 1H), 7.18 (d, J=8.8 Hz, 2H), 5.16 (s, 2H), 3.86 (s, 3H). FD mass spec 441. Anal. Calcd. for C$_{22}$H$_{17}$O$_3$SBr: C, 59.87; H, 3.88. Found: C, 60.13; H, 4.10.

Step d): [6-Methoxy-3-[4-[2-(1-piperidinyl)ethoxy]phenoxy]-2-(4-benzyloxyphenyl)]benzo[b]thiophene-(S-oxide)

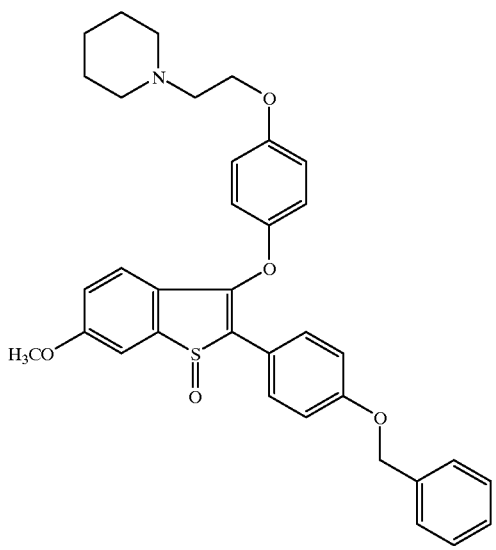

The title compound was obtained as a yellow solid, mp 89–93° C. $^1$H NMR (DMSO-d$_6$) d 7.68 (d, J=2.2 Hz, 1H), 7.62 (d, J=8.8 Hz, 2H), 7.42–7.28 (m, 5H), 7.08–6.92 (m, 6H), 6.86 (d, J=8.8 Hz, 2H), 5.09 (s, 2H), 3.94 (bt, J=5.8 Hz, 2H), 3.81 (s, 3H), 2.56 (bt, J=5.8 Hz, 2H), 2.37–2.34 (m, 4H), 1.45–1.31 (m, 6H). FD mass spec 592. Anal. Calcd. for C$_{35}$H$_{35}$NO$_5$S·0.25 EtOAc: C, 71.62; H, 6.18; N, 2.32. Found: C, 71.32; H, 5.96; N, 2.71.

Step e): [6-Methoxy-3-[4-[2-(1-piperidinyl)ethoxy]phenoxy]-2-(4-benzyloxyphenyl)]benzo[b]thiophene

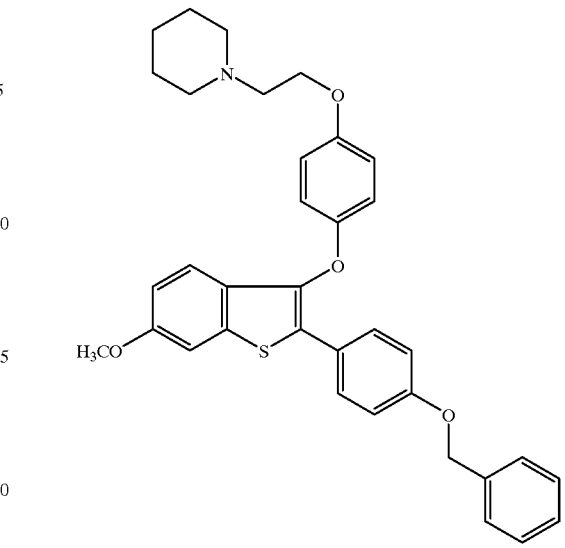

The title compound was obtained in 91% yield, mp 106–110° C. $^1$H NMR (DMSO-d$_6$) d 7.59 (d, J=8.8 Hz, 2H), 7.54 (d, J=2.2 Hz, 1H), 7.42–7.28 (m, 5H), 7.13 (d, J=8.8 Hz, 1H), 7.03 (d, J=8.8 Hz, 2H), 6.82 (s, 4H), 5.08 (s, 2H), 3.92 (bt, J=5.8 Hz, 2H), 3.78 (s, 3H), 2.55 (bt, J=5.8 Hz, 2H), 2.37–2.33 (m, 4H), 1.44–1.31 (m, 4H). FD mass spec 565. Anal. Calcd. for C$_{35}$H$_{35}$NO$_4$S: C, 74.31; H, 6.24; N, 2.48. Found: C, 74.26; H, 6.17; N, 2.73.

Step f): Preparation of [6-methoxy-3-[4-[2-(1-piperidinyl)ethoxy]phenoxy]-2-(4-hydroxyphenyl)]benzo[b]thiophene

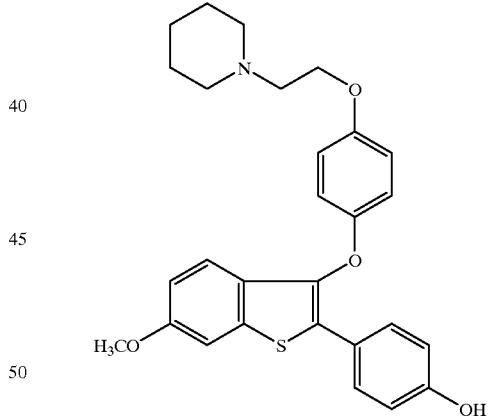

The title compound was obtained in 88% yield, mp 147–150° C. $^1$H NMR (DMSO-d$_6$) d 9.72 (s, 1H), 7.51 (d, J=2.0 Hz, 1H), 7.48 (d, J=8.6 Hz, 2H), 7.11 (d, J=8.8 Hz, 1H), 6.88 (dd, J=8.8, 2.2 Hz, 1H), 6.81 (s, 4H), 6.76 (d, J=8.6 Hz, 2H), 3.91 (bt, J=5.9 Hz, 2H), 3.77 (s, 3H), 2.55 (bt, J=5.9 Hz, 2H), 2.38–2.33 (m, 4H), 1.46–1.28 (m, 6H). FD mass spec 475. Anal. Calcd. for C$_{28}$H$_{29}$NO$_4$S: C, 70.71; H, 6.15; N, 2.94. Found: C, 71.00; H, 6.17; N, 2.94.

EXAMPLE 17

Preparation of [6-methoxy-3-[4-[2-(1-piperidinyl)ethoxy]phenoxy]-2-(4-hydroxyphenyl)]benzo[b]thiophene hydrochloride

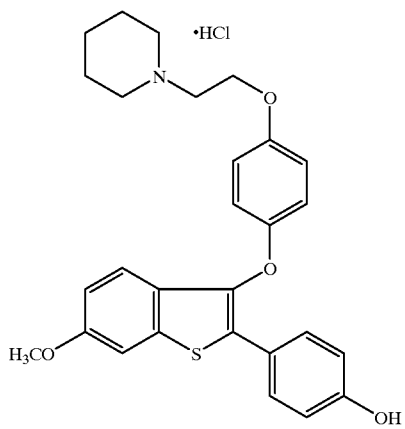

The title compound was prepared in a manner analogous to that employed in Example 15 to yield the title compound, mp 215–217° C. $^1$H NMR (DMSO-$d_6$) d 10.28 (bs, 1H), 9.80 (s, 1H), 7.52 (d, J=2.2 Hz, 1H), 7.47 (d, J=8.6 Hz, 2H), 7.12 (d, J=8.4 Hz, 1H), 6.91–6.80 (m, 5H), 6.78 (d, J=8.6 Hz, 2H), 4.27 (bt, J=5.8 Hz, 2H), 3.78 (s, 3H), 3.43–3.34 (m, 4H), 2.97–2.91 (m, 2H), 1.78–1.61 (m, 5H), 1.36–1.29 (m, 1H). FD mass spec 475. Anal. Calcd. for $C_{28}H_{29}NO_4S\cdot1.0$ HCl: C, 65.68; H, 5.90; N, 2.73. Found: C, 65.87; H, 5.79; N, 2.99.

FORMULATION EXAMPLES

In the formulations which follow, "active ingredient" means a compound of formula I, or a salt or solvate thereof.

| Formulation Example 1 Gelatin Capsules | |
|---|---|
| Ingredient | Quantity (mg/capsule) |
| Active ingredient | 0.1–1000 |
| Starch, NF | 0–650 |
| Starch flowable powder | 0–650 |
| Silicone fluid 350 centistokes | 0–15 |

| Formulation Example 2 Tablets | |
|---|---|
| Ingredient | Quantity (mg/tablet) |
| Active ingredient | 2.5–1000 |
| Cellulose, microcrystalline | 200–650 |
| Silicon dioxide, fumed | 10–650 |
| Stearate acid | 5–15 |

| Formulation Example 3 Tablets | |
|---|---|
| Ingredient | Quantity (mg/tablet) |
| Active ingredient | 25–1000 |
| Starch | 45 |
| Cellulose, microcrystalline | 35 |
| Polyvinylpyrrolidone | 4 |

-continued

| Formulation Example 3 Tablets | |
|---|---|
| Ingredient | Quantity (mg/tablet) |
| (as 10% solution in water) Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

| Formulation Example 4 Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No.45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

| Formulation Example 5 Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

| | Formulation Example 6 Suppositories | |
|---|---|---|
| Ingredient | | Quantity (mg/suppository) |
| Active ingredient | | 250 |
| Saturated fatty acid glycerides | | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

| Formulation Example 7 Injectable Formulations | |
|---|---|
| Ingredient | Quantity |
| Active ingredient | 50 mg |
| Isotonic saline | 1,000 mL |

The solution of the above ingredients is intravenously administered to a patient at a rate of about 1 mL per minute.

We claim:

1. A method of treating, in a patient in need of such treatment, Alzheimer's disease comprising administering a therapeutically effective amount of a compound having the structure

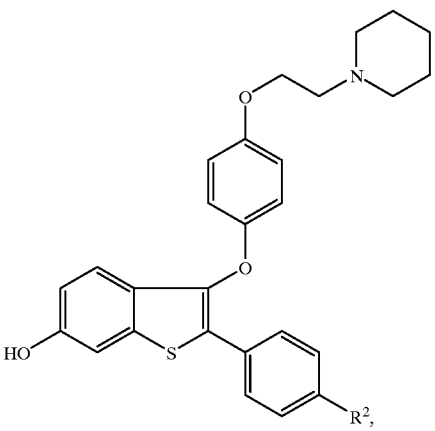

or a pharmaceutically acceptable salt or pro-drug thereof, wherein $R^2$ is hydroxy or methoxy.

2. The method of claim 1 wherein said compound is 6-hydroxy-2-(4-methoxyphenyl)-3-[4-(2-piperidinoethoxy) phenoxy]benzo[b]thiophene or a pharmaceutically acceptable salt thereof.

3. The method of claim 1 wherein said compound is 6-hydroxy-2-(4-hydroxyphenyl)-3-[4-(2-piperidinoethoxy) phenoxy]benzo[b]thiophene or a pharmaceutically acceptable salt thereof.

4. The method of claim 1 wherein said salt is the hydrochloride salt.

5. The method of claim 1 wherein said patient is a woman.

* * * * *